United States Patent
Phan et al.

(10) Patent No.: US 6,420,535 B1
(45) Date of Patent: Jul. 16, 2002

(54) 6-O-CARBAMATE KETOLIDE DERIVATIVES

(75) Inventors: Ly Tam Phan, Park City, IL (US); Yat Sun Or, Cambridge, MA (US); Zhenkun Ma, Gurnee, IL (US); Yan Chen, Guilford, CT (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/577,645

(22) Filed: May 24, 2000

Related U.S. Application Data

(60) Provisional application No. 60/137,976, filed on Jun. 7, 1999.

(51) Int. Cl.$^7$ .......................... C07H 17/08; C07H 1/00; C07G 17/00; A01N 1/00
(52) U.S. Cl. ........................ 536/7.2; 536/7.4; 536/124; 536/125; 514/29
(58) Field of Search .................. 536/7.2, 7.4, 124, 536/125; 514/29

(56) References Cited

U.S. PATENT DOCUMENTS

| | | | |
|---|---|---|---|
| 4,331,803 A | | 5/1982 | Watanabe et al. |
| 4,670,549 A | | 6/1987 | Morimoto et al. |
| 4,680,368 A | | 7/1987 | Nakamoto et al. |
| 4,826,820 A | | 5/1989 | Brain |
| 4,990,602 A | | 2/1991 | Morimoto et al. |
| 5,444,051 A | | 8/1995 | Agouridas et al. |
| 5,527,780 A | | 6/1996 | Agouridas et al. |
| 5,614,614 A | | 3/1997 | Agouridas et al. |
| 5,750,510 A | * | 5/1998 | Elliott et al. .................. 514/29 |
| 5,770,579 A | | 6/1998 | Agouridas et al. |
| 5,866,549 A | * | 2/1999 | Or et al. ........................ 514/29 |
| 6,034,069 A | * | 3/2000 | Or et al. ........................ 514/29 |
| 6,100,240 A | * | 8/2000 | Cheng et al. .................. 514/29 |
| 6,147,197 A | * | 11/2000 | Or et al. ........................ 536/7.2 |

FOREIGN PATENT DOCUMENTS

| | | | |
|---|---|---|---|
| EP | 0216169 | 4/1987 | |
| EP | 0260948 | 6/1992 | |
| EP | 0559896 | 9/1993 | |
| EP | 0596802 | 5/1994 | |
| EP | 0 619320 A1 | * 12/1994 | ........... C07H/17/08 |
| WO | 9209614 | 6/1992 | |
| WO | 9710251 | 3/1997 | |

OTHER PUBLICATIONS

T. Green and P. Wuts, Protective Groups in Organic Synthesis, $2^{nd}$ ed., John Wiley & Sons, Inc. (1991).
Roche, ed. Bioreversible Carriers in Drug Design, American Pharmaceutical Assoc. and Pergamon Press, 1987.
Baker, et al., J. Org. Chem., 53, 2340 (1988).
Organic Reactions, 27: 345–390 (1982).
Chemical Reviews, vol. 95, No. 7, 2457–2483 (1995).
K. Sonogashira, et al., Tetrahedron Letters, No. 50, 4467–4470 (1975).

* cited by examiner

*Primary Examiner*—Jezia Riley
(74) *Attorney, Agent, or Firm*—B. Gregory Donner

(57) ABSTRACT

The invention relates to a novel 6-O-carbamate ketolide compound or a pharmaceutically acceptable salt, ester, solvate or prodrug thereof, to a composition comprising the compound and a suitable carrier, a method of preparing the compound, and a method of treatment and prevention of infections in a mammal.

14 Claims, No Drawings

6-O-CARBAMATE KETOLIDE DERIVATIVES

REFERENCE TO RELATED APPLICATION

This application is a conversion of U.S. Provisional Application Ser. No. 60/137,976 filed on Jun. 7, 1999 now abandoned.

TECHNICAL FIELD

The present invention relates to a novel macrolide compound or a pharmaceutically acceptable salt, ester, solvate or prodrug thereof, to a composition comprising the compound and a suitable carrier, a method of preparing the compound, and a method of treatment and prevention of infections in a mammal.

BACKGROUND OF THE INVENTION

Erythromycins A, B, C and D, represented by formula (I),

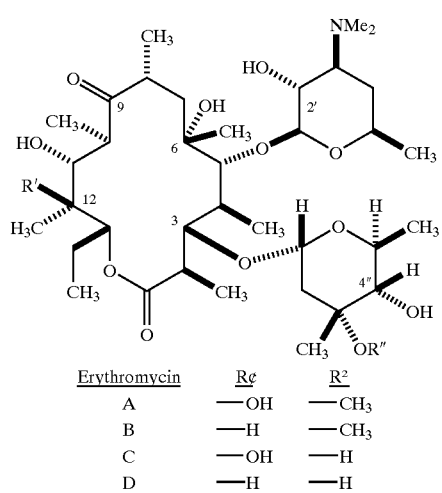

| Erythromycin | $R^c$ | $R^2$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

U.S. Pat. No. 5,444,051 and U.S. Pat. No. 5,770,579 disclose 6-O-substituted-3-oxoerythromycin derivatives in which the substituents are selected from alkyl, —CONH$_2$, —CONHC(O)alkyl and —CONHSO$_2$alkyl. PCT application WO 97/10251, published Mar. 20, 1997, discloses 6-O-methyl 3-descladinose erythromycin derivatives.

European Patent Application 0216169, published Apr. 1, 1987, discloses erythromycin A 6-carbamate derivatives.

European Patent Application 596802, published May 11, 1994, discloses bicyclic 6-O-methyl-3-oxoerythromycin A derivatives.

PCT application WO 92/09614, published Jun. 11, 1992, discloses tricyclic 6-O-methylerythromycin A derivatives.

SUMMARY OF THE INVENTION

In one aspect, the invention relates to a compound represented by a formula selected from the group consisting of:

a compound of the formula

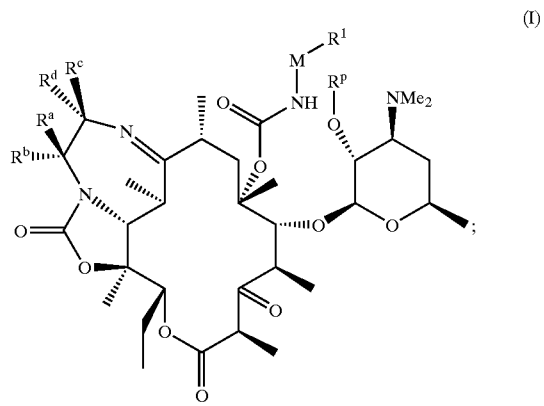

a compound of the formula

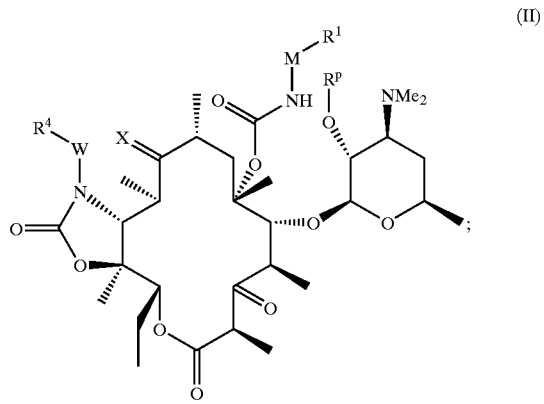

a compound of the formula

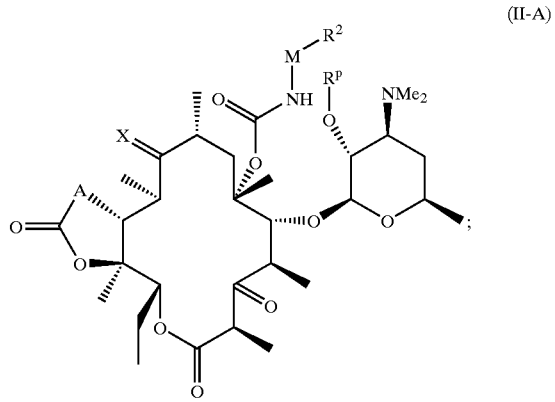

a compound of the formula
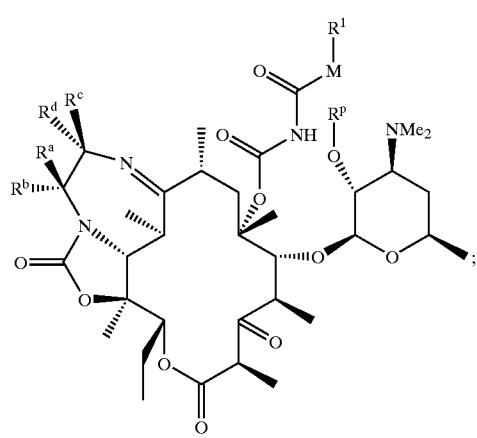
(III)
a compound of the formula
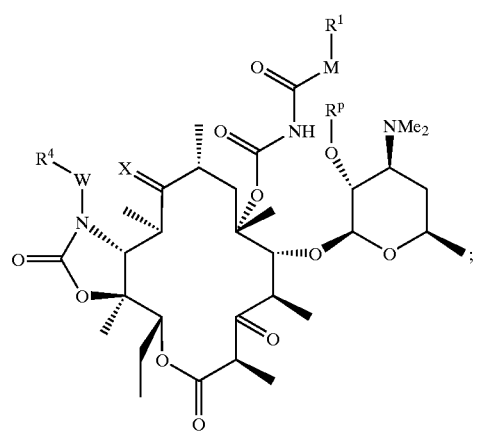
(IV)
a compound of the formula
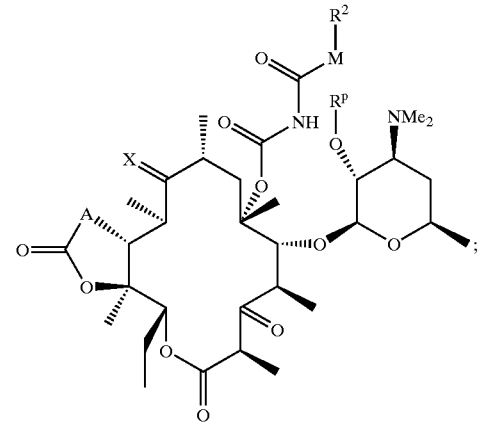
(IV-A)
a compound of the formula
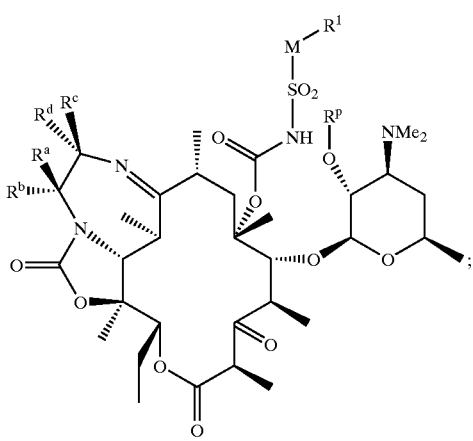
(V)
a compound of the formula
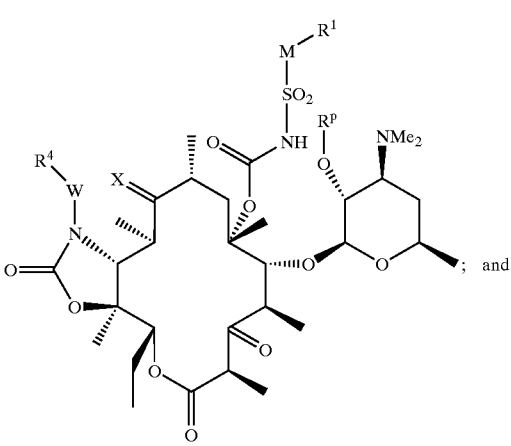
(VI)
a compound of the formula
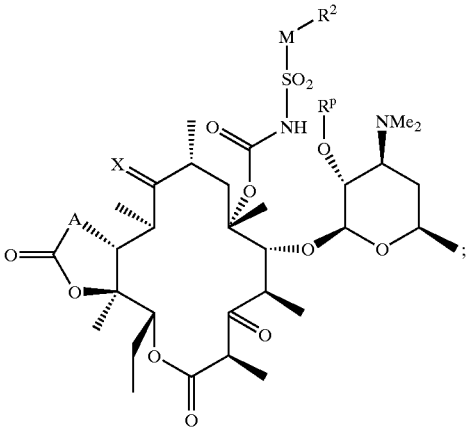
(VI-A)

or a pharmaceutically acceptable salt, solvate, ester, or prodrugs thereof, wherein:

$R^p$ is hydrogen or a hydroxy protecting group;

A is —O— or —NH—;

M is either absent or selected from the group consisting of:
(a) —(CH$_2$)$_l$— where l is 1 to 5,
(b) —(CH$_2$)$_m$—CH=CH— where m is 0 to 3,
(c) —(CH$_2$)$_n$—C≡C— where n is 0 to 3;

$R^1$ is selected from the group consisting of:
(a) hydrogen,
(b) aryl,
(c) substituted aryl,
(d) heteroaryl,
(e) substituted heteroaryl, and
(f) Ar$_1$—Ar$_2$ wherein Ar$_1$ and Ar$_2$ are independently selected from the group consisting of:
(i) aryl,
(ii) substituted aryl,
(iii) heteroaryl, and
(iv) substituted heteroaryl;

R is selected from the group consisting of:
(a) aryl,
(b) substituted aryl,
(c) heteroaryl,
(d) substituted heteroaryl, and
(e) Ar$_1$—Ar$_2$ wherein Ar$_1$ and Ar$_2$ are independently selected from the group consisting of:
(i) aryl,
(ii) substituted aryl,
(iii) heteroaryl, and
(iv) substituted heteroaryl;

X is selected from the group consisting of:
(a) O
(b) N—OH
(c) N—O—U—R$^3$ wherein U is selected from the group consisting of:
(i) —C(O)—
(ii) —C$_1$–C$_6$ alkyl,
(iii) —C$_1$–C$_6$ alkenyl, and
(iv) —C$_1$–C$_6$ alkynyl,
and R$^3$ is selected from the group consisting of:
(i) hydrogen,
(ii) aryl,
(iii) substituted aryl,
(iv) heteroaryl,
(v) substituted heteroaryl, and
(vi) Ar$_1$—Ar$_2$ wherein Ar$_1$ and Ar$_2$ are independently selected from the group consisting of:
(1) aryl,
(2) substituted aryl,
(3) heteroaryl, and
(4) substituted heteroaryl;

W is selected from the group consisting of
(a) —NH—(CH$_2$)$_p$— wherein p is 0 to 5,
(b) —(CH$_2$)$_q$— wherein q is 0 to 5,
(c) —O—(CH$_2$)$_r$— wherein r is 0 to 5,
(d) —NH—C$_1$–C$_6$ alkenyl-,
(e) —C$_1$–C$_6$ alkenyl-,
(f) —O—C$_1$–C$_6$ alkenyl-,
(g) —NH-C$_1$–C$_6$ alkynyl-,
(h) —C$_1$–C$_6$ alkynyl-, and
(i) —O-C$_1$–C$_6$ alkynyl-, $R^4$ is selected from the group consisting of:
(a) hydrogen,
(b) aryl,
(c) substituted aryl,
(d) heteroaryl,
(e) substituted heteroaryl, and
(f) Ar$_1$—Ar$_2$ wherein Ar$_1$ and Ar$_2$ are independently selected from the group consisting of:
(i) aryl,
(ii) substituted aryl,
(iii) heteroaryl, and
(iv) substituted heteroaryl; and $R^a$, $R^b$, $R^c$ and $R^d$ are independently selected from the group consisting of:
(a) hydrogen;
(b) C$_1$–C$_6$ alkyl, optionally substituted with one or more substituents selected from the group consisting of:
(i) —L—M—R$^1$ or —L—M—R$^2$, wherein M, R$^1$, and R$^2$ are as defined above, and L is either absent or selected from the group consisting of:
(1) —C(O)NH—;
(2) —NHC(O)—;
(3) —NH—;
(4) —N(CH$_3$)—;
(5) —O—;
(6) —S(O)$_x$—, wherein x is 0, 1, or 2;
(7) —C(=NH)NH—;
(8) —C(O)O—;
(9) —OC(O)—;
(10) —OC(O)NH—;
(11) —NHC(O)O—; and
(12) —NHC(O)NH—; and
(ii) halogen;
(c) C$_3$–C$_7$ cycloalkyl;
(d) heterocycloalkyl; and
(e) substituted heterocycloalkyl;
or any one pair of substituents selected from the group consisting of $R^aR^b$, $R^aR^c$, $R^aR^d$, $R^bR^c$, $R^bR^d$ or $R^cR^d$ taken together with the atom or atoms to which they are attached form a 3- to 7- membered ring optionally containing a hetero function selected from the group consisting of —O—; —NH—; —N(C$_1$–C$_6$ alkyl-)—; —N(aryl-C$_1$-C$_6$ alkyl-)—; —N(substituted aryl-C$_1$-C$_6$ alkyl-)—; —N(heteroaryl-C$_1$–C$_6$ alkyl-)—; —N(substituted heteroaryl-C$_1$–C$_6$ alkyl-)—; —S(O)$_x$—, wherein x is 0, 1, or 2; —C(O)—NH—; —NH—C(O)—; —C(O)—NR$^{12}$—; and —NR$^{12}$—C(O)—; wherein R$^{12}$ is hydrogen, C$_1$–C$_3$ alkyl, C$_1$–C$_3$ alkyl substituted with aryl, substituted aryl, heteroaryl, or substituted heteroaryl.

In another aspect, the invention relates to a process for preparing a compound of formula I, II, II-A, III, IV, IV-A, V, VI, and VI-A, as defined above, comprising the steps of:

(a) reacting a compound having a formula:

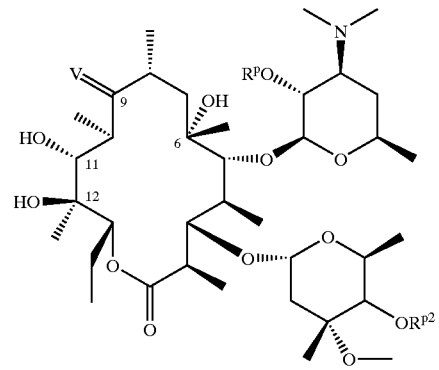

wherein V is selected from the group consisting of:

(i) O,
(ii) N—O—(CH$_2$)$_s$—R$^x$, wherein s is 0 to 5 and R$^x$ is selected from the group consisting of:
   (1) hydrogen,
   (2) alkyl,
   (3) substituted alkyl,
   (4) aryl,
   (5) substituted aryl,
   (6) heteroaryl, and
   (7) substituted heteroaryl,
(iii) N—O—C(O)—(CH$_2$)$_s$—R$^x$, wherein s and R$^x$ is as defined above,
(iv) N—O—C(R$^y$)(R$^z$)—O—R$^x$, wherein R$^x$ is as defined above, and R$^y$ and R$^z$ are independently selected from the group consisting of:
   (1) hydrogen,
   (2) unsubstituted C$_1$–C$_{12}$-alkyl,
   (3) C$_1$–C$_{12}$-alkyl substituted with aryl, and
   (4) C$_1$–C$_{12}$-alkyl substituted with substituted aryl,
   or R$^y$ and R$^z$ taken together with the carbon to which each is attached form a C$_3$–C$_{12}$-cycloalkyl ring; and R$^P$ and R$^{P2}$ are as defined above;
   with either (i) an isocyanate reagent of the formula O=C=N—M—R$^1$, O=C=N—M—R$^2$, O=C=N—C(O)—M—R$^1$, O=C=N—C(O)—M—R$^2$, O=C=N—S(O)$_2$—M—R$^1$, or O=C=N—S(O)$_2$—M—R$^2$, wherein M, R$^1$, and R$^2$ are as defined above, or (ii) an activated isocyanate derivative followed by an alkylation with a compound of the formula X$_1$—M—R$^1$ or X$_1$—M—R$^2$, wherein M, R$^1$, and R$^2$ are as defined above, and X$_1$ is a halide or a leaving group, and optionally removing the activating group;
(b) carrying out one or more of the following steps in any suitable order:
   (i) removing any hydroxy protecting group that may be present;
   (ii) removing a protecting group on the C9-oxime;
   (iii) converting the C9-oxime into a keto moiety;
   (iv) removing the cladinose sugar and oxidizing the resulting hydroxy group;
   (v) converting the 11,12-diol into an 11,12-carbonate;
   (vi) converting the 11,12-diol into an 11,12-carbamate optionally substituted on the nitrogen atom; and
   (vi) preparing a tricyclic imine derivative from the 11,12-carbamate.

In a preferred process, the 11,12-carbonate is prepared by treating the compound of the formula:

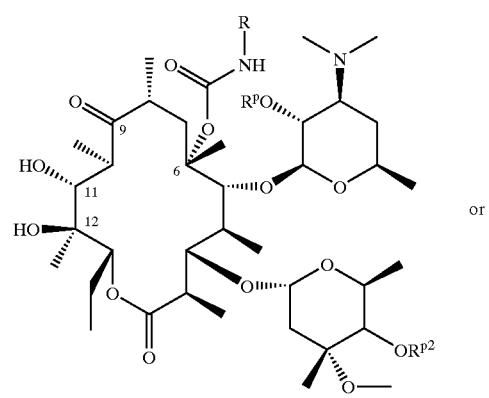

or

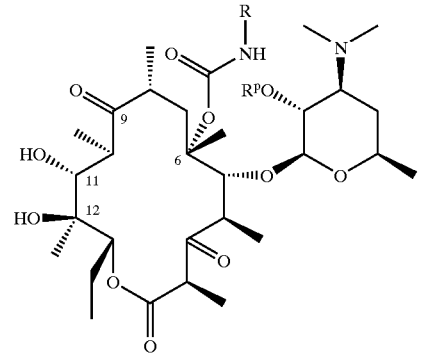

wherein R is selected from the group consisting of —M—R$^1$, —M—R$^2$, —C(O)—M—R$^1$, —C(O)—M—R$^2$, —S(O)$_2$—M—R$^1$, —S(O)$_2$—M—R$^2$, with carbonyldiimidazole and sodium hexamethyldisilazide and optionally removing the 2'-hydroxy group.

In another preferred process, the 11,12-carbamate optionally substituted on the nitrogen atom is prepared by the steps of:

(a) treating the compound of the formula:

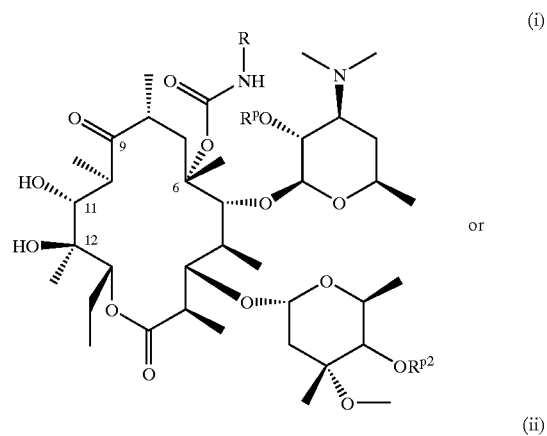

(i)

or

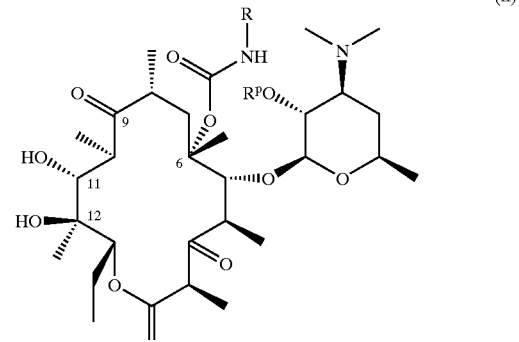

(ii)

wherein R is selected from the group consisting of —M—R$^1$, —M—R$^2$, —C(O)—M—R$^1$, —C(O)—M—R$^2$, —S(O)$_2$—M—R$^1$, —S(O)$_2$—M—R$^2$, optionally with a reagent combination selected from the group consisting of:
   (1) an alkali metal hydride and a phosgene reagent selected from phosgene, diphosgene and triphosgene under anhydrous conditions, followed by a base catalyzed decarboxylation, and
   (2) reaction with methanesulfonic anhydride in pyridine, followed by treatment with an amine base, (b) treating the compound of formula (i) or (ii) or the compound obtained in step (a) with an alkali metal hydride base and carbonyldiimidazole;

(c) reacting the compound obtained in step (b) with an amine of the formula $H_2N$—W—$R^4$, wherein W and $R^4$ are as defined above, anhydrous ammonia, or ammonium hydroxide;

(d) optionally removing the cladinose sugar and oxidizing the resulting hydroxy group; and (e) optionally removing any hydroxy protecting group that may be present.

In another preferred process, the tricyclic imine is prepared by the steps of:

(a) treating a compound of the formula:

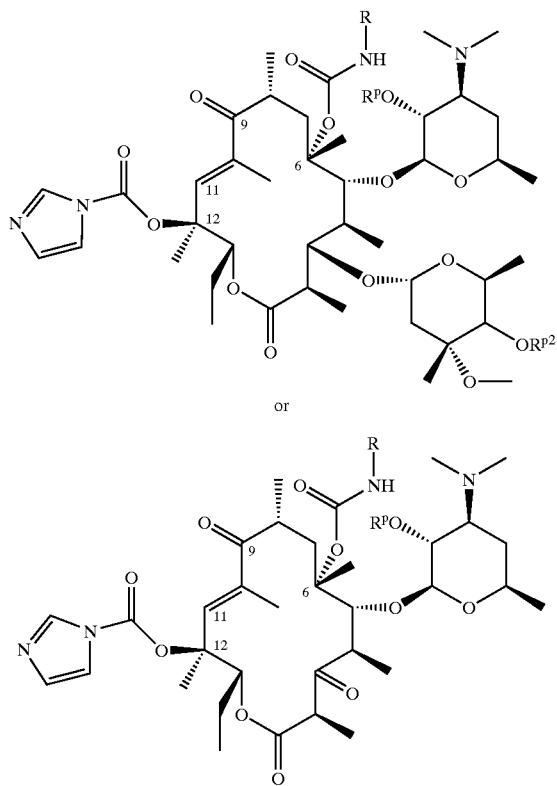

or wherein R is as defined above, with a diamine of the formula:

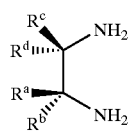

wherein $R^a$, $R^b$, $R^c$ and $R^d$, are as previously defined;

(b) cyclizing the compound obtained in step (a);

(c) optionally removing the cladinose sugar and oxidizing the resulting hydroxy group; and (d) optionally removing any hydroxy protecting group that may be present.

In yet another aspect, the invention relates to a pharmaceutical composition comprising a compound as described above and a pharmaceutically acceptable carrier.

Yet another aspect of the invention relates to a method of treating a bacterial infection comprising administering a therapeutically effective amount of a compound of the invention to a patient in need of such treatment.

DETAILED DESCRIPTION OF THE INVENTION

Definitions

The terms "$C_1$–$C_6$ alkyl" as used herein refer to saturated, straight, or branched chain hydrocarbon radicals derived from a hydrocarbon moiety containing between one and six carbon atoms by removal of a single hydrogen atom. In general, a group denoted as $C_x$–$C_y$, wherein x and y are integers, refers to a group of x to y carbon atoms. For example, the group $C_x$–$C_y$ alkyl, wherein x is 1 and y is 3, includes $C_1$–$C_3$ alkyl radicals such as methyl, ethyl, propyl, and isopropyl. Exemplary $C_1$–$C_6$alkyl radicals include methyl, ethyl, propyl, isopropyl, n-butyl, tert-butyl, neopentyl, and n-hexyl. Examples of $C_1$–$C_{12}$ alkyl radicals include all the foregoing examples, as well as n-heptyl, n-octyl, n-nonyl, n-decyl, n-undecyl, and n-docecyl.

The term "$C_1$–$C_6$ alkenyl" as used herein refers to straight- or branched-chain hydrocarbon radicals comprising one to six carbon atoms, respectively, which contain one or more carbon-carbon double bonds. Compounds of the invention have either a known configuration or exist as a mixture of isomers.

The term "$C_1$–$C_6$ alkynyl" used herein refers to straight- or branched-chain hydrocarbon radicals comprising one to six carbon atoms, respectively, which contain one or more carbon-carbon triple bonds. Compounds of the invention have either a known configuration or exist as a mixture of isomers.

The term "aryl" as used herein refers to a mono-, fused bicyclic or fused tricyclic carbocyclic ring system having one or more aromatic rings including, but not limited to, phenyl, naphthyl, indanyl, indenyl, tetrahydronaphthyl, anthracenyl, phenanthrenyl, biphenylenyl, fluorenyl, and the like.

The term "substituted aryl" as used herein refers to an aryl group as defined herein substituted by independent replacement of one, two or three of the hydrogen atoms thereon with Cl, Br, F, I, OH, CN, $C_1$–$C_3$ alkyl, $C_1$–$C_6$ alkoxy, $C_1$–$C_6$ alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group. Substituents also include alkenyloxy, for example, methylenedioxy and ethylenedioxy. The substituted aryl groups also include tetrafluorophenyl and pentafluorophenyl.

The terms "halo", "halide", and "halogen" as used herein refer to an atom selected from fluorine, chlorine, bromine, and iodine.

The term "heteroaryl" as used herein refers to a cyclic aromatic radical having from five to ten ring atoms of which one ring atom is selected from S, O and N; one, two, or three ring atoms may be additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, tetrazolyl, thiophenyl, furanyl, quinolinyl, isoquinolinyl, and the like.

The term "heterocyclic", "heterocycle", and "heterocycloalkyl" as used herein refers to a non-aromatic partially unsaturated or fully saturated 3- to 10-membered ring system which includes single rings of 3 to 8 atoms in size and bi- or tri-cyclic ring systems which may include aromatic six-membered aryl or heteroaryl rings fused to a non-aromatic ring. These heterocyclic rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heteroaryl" as used herein refers to a heteroaryl group as defined above substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkyl, thioalkoxy, alkoxy, alkoxyalkoxy, amino, alkylamino, dialkylamino, mercapto, —$SO_3H$, nitro, carboxaldehyde, carboxy, alkoxycarbonyl and carboxamide. In addition, any one substitutent may be an aryl, arylalkyl, cycloalkyl, heteroaryl, or heterocycloalkyl group.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, $C_1$–$C_3$ alkyl, $C_1$–$C_6$ alkoxy, $C_1$–$C_6$ alkoxy substituted with aryl, haloalkoxy, thioalkoxy, amino, alkylamino, dialkylamino, mercapto, nitro, carboxaldehyde, carboxy, alkoxycarbonyl and carboxamide. In addition, any one substitutent may be an aryl, heteroaryl, or heterocycloalkyl group.

The term "hydrocarbyl" as used herein refers to an alkyl, alkenyl, or alkynyl group as described above. Preferably, hydrocarbyl groups have from one to six carbon atoms as defined for $C_1$–$C_6$ alkyl, $C_1$–$C_6$ alkenyl, and $C_1$–$C_6$ alkynyl groups as described above.

The term "hydroxy-protecting group" as used herein refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, c.f., for example T. H. Wiley & Sons, New York (1991). Examplary hydroxy-protecting groups are methylthiomethyl, tert-dimethylsilyl, tert-butyldiphenylsilyl, acyl substituted with an aromatic group, and the like.

The term "protected hydroxy" as used herein refers to a hydroxy group protected with a hydroxy protecting group as defined above including, but not limited to, benzoyl, acetyl, trimethylsilyl, triethylsilyl, methoxymethyl, and the like.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66: 1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Numerous asymmetric centers may exist in the compounds of the present invention. Except where otherwise noted, the present invention contemplates the various stereoisomers and mixtures thereof.

A preferred compound of the invention is represented by a formula:

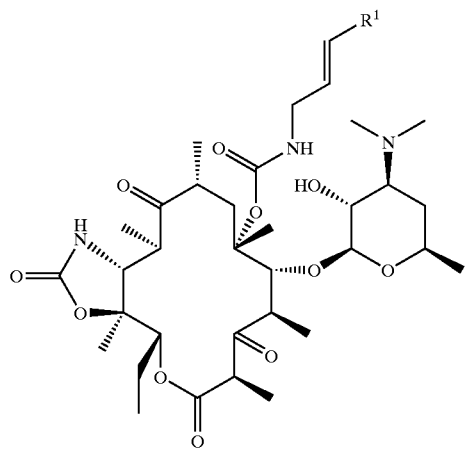

(IX)

wherein R¹ is as previously defined.

Another preferred compound of the invention is represented by a formula:

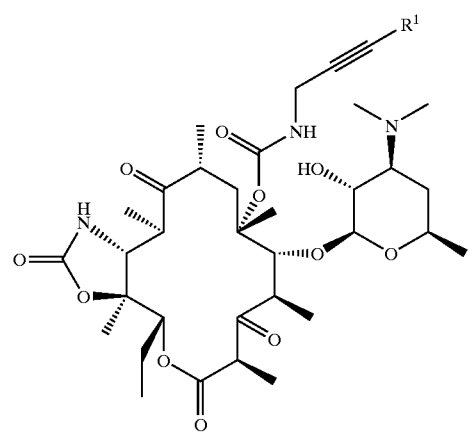

(X)

wherein R¹ is as previously defined.

An additional preferred compound of the invention is represented by a formula:

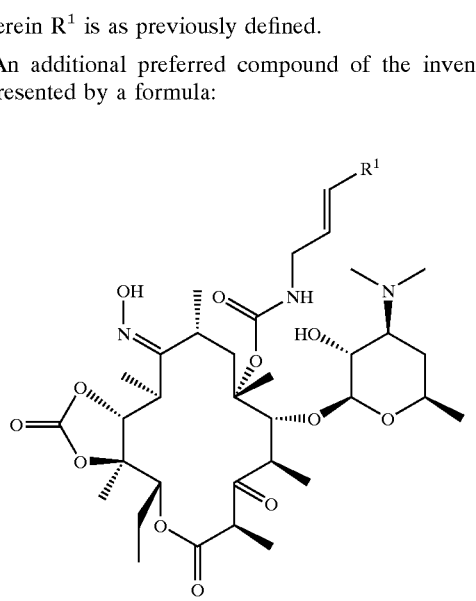

(XI)

wherein R¹ is as previously defined.

Yet another preferred compound is represented by a formula:

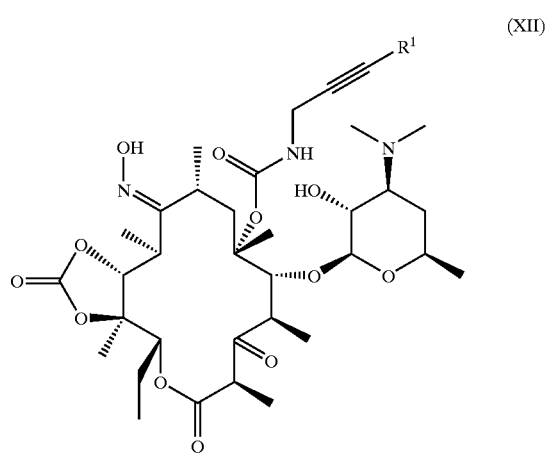

(XII)

wherein R¹ is as previously defined.

Still another preferred compound is represented by a formula:

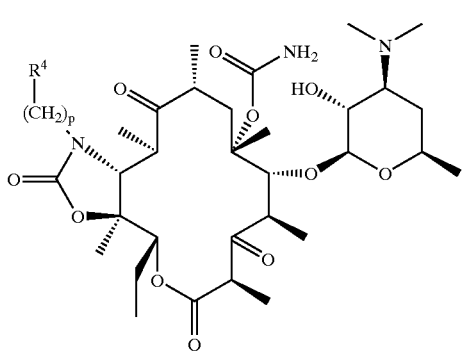

(XIII)

wherein R⁴ is as previously defined and p is 0 to 5.

Still another additional compound is represented by a formula:

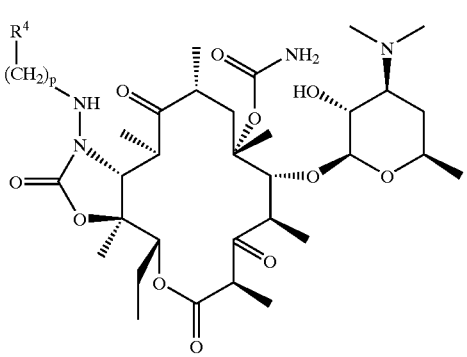

(XIV)

wherein R⁴ is as previously defined and p is 0 to 5.

Representative compounds of the invention include, but are not limited to the following.

Compound of formula (IV-A): wherein A is —O—; X is N—OH; —M— is absent; R² is phenyl; and Rp is hydrogen;

Compound of formula (II-A): wherein A is —O—; X is N—OH; —M— is absent; R² is hydrogen; and $R^p$ is hydrogen;

Compound of formula (II-A): wherein A is —O—; X is N—OH; —M— is —CH$_2$—CH=CH—; R$^2$ is 3-quinolyl; and R$^p$ is hydrogen;

Compound of formula (II): wherein W is absent, R$^4$ is H; X is O; —M— is —CH$_2$-CH=CH— R$^1$ is hydrogen; and R$^p$ is hydrogen; and Compound of formula (II-A): wherein A is —NH—; X is O; —M— is -CH$_2$—CH=CH—; R$^2$ is 3-quinolyl; and R$^p$ is hydrogen.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eyd ns are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more, such as from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of a compounds of the invention per day in a single or multiple doses.

Abbreviations

Abbreviations which have been used in the descriptions of the scheme and the examples that follow are: AIBN for azobisisobutyronitrile; $Bu_3SnH$ for tributyltin hydride; CDI for carbonyldiimidazole; DBU for 1,8-diazabicyclo[5.4.0] undec-7-ene; DEAD for diethylazodi-carboxylate; DMF for dimethylformamide; DMSO for dimethylsulfoxide; DPPA for diphenylphosphoryl azide; $Et_3N$ for triethylamine; EtOAc for ethyl acetate; $Et_2O$ for diethyl ether; EtOH for ethanol; HOAc for acetic acid; MeOH for methanol; NaN $(TMS)_2$ for sodium bis(trimethylsilyl)amide; NCS for N-chlorosuccinimide; NMMO for N-methylmorpholine N-oxide; $Me_2S$ for dimethyl sulfide; TEA for triethylamine; THF for tetrahydrofuran; and TPP for triphenylphosphine. Starting materials, reagents, and solvents are available from Aldrich Chemical Company (Milwaukee, Wis.) unless otherwise noted herein.

Synthetic Methods

The compounds and processes of the present invention will be better understood in connection with the following synthetic Schemes, which illustrate the methods by which the compounds of the invention may be prepared. The compounds of formulae I, II, II-A, III, IV, IV-A, V, VI, and VI-A may be prepared by a variety of synthetic routes. Representative procedures are shown below in Schemes 1–8. The groups A, M, X, W, $R^1$, $R^2$, $R^3$, $R^4$, $R^a$, $R^b$, $R^c$, $R^d$, $R^p$, and $R^{p2}$ are as previously defined unless otherwise noted. It will be readily apparent to one of ordinary skill other compounds of formulae I, II, II-A, III, IV, IV-A, V, VI, and VI-A can be synthesized by substitution of the appropriate reactants and agents in the syntheses shown below. It will also be apparent to one skilled in the art that the selective protection and deprotection steps, as well as the order of the steps themselves, can be carried out in varying order, depending on the nature of the substrate compound and the groups A, M, X, W, $R^1$, $R^2$, $R^3$, $R^4$, $R^p$, and $R^{p2}$.

The conversion of erythromycin A (available from Abbott Laboratories, Abbott Park, Ill.) to 1 is described in U.S. Pat. Nos. 4,990,602; 4,331,803; 4,680,368; and 4,670,549; and European Patent Application EP 260,938, the disclosures of which are herein incorporated by reference. The C-9-carbonyl group of the erythromycin A is typically protected as an oxime 1, wherein V is N—O—$(CH_2)_s$—$R^x$, N—O—C(O)—$(CH_2)_s$—$R^x$, or N—O—$C(R^y)(R^z)$—O—$R^x$, wherein s is 0 to 5 and $R^x$ is (a) hydrogen, (b) alkyl, (c) substituted alkyl, (d) aryl, (e) substituted aryl,
(f) heteroaryl, and (g) substituted heteroaryl, and wherein $R^y$ and $R^z$ are independently selected from (a) hydrogen, (b) unsubstituted $C_1-C_{12}$-alkyl, (c) $C_1-C_{12}$-alkyl substituted with aryl, and
(d) $C_1-C_{12}$-alkyl substituted with substituted aryl, or $R^y$ and $R^z$ taken together with the carbon to which they are attached form a $C_3-C_{12}$-cycloalkyl ring. A preferred protected oxime group V is N—O—(1-isopropoxycyclohexyl) or N—O—C(O)-phenyl (i.e. N—O—benzoyl).

The 2'- and 4"-hydroxy groups of the C-9 protected erythromycin A can be treated with a suitable hydroxy protecting reagent in an aprotic solvent. Hydroxy protecting reagents include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, DMF, tetrahydrofuran (THF), N-methyl pyrrolidinone, dimethylsulfoxide, diethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran, N-methyl pyrrolidinone or a mixture thereof. The protection of the 2'- and optionally the 4"-hydroxy groups of the C-9 protected erythromycin A may be accomplished sequentially or simultaneously. The variables $R^P$ and $R^{P2}$ denote a hydroxy protecting group when used throughout the specification in the structural formulas. Preferred protecting groups include, but are not limited to, acetyl, trimethylsilyl, and benzoyl. A thorough discussion of protecting groups and the solvents in which they are most effective is provided by T. W. Greene and P. G. M. Wuts in *Protective Groups in Organic Synthesis*, 2nd ed., John Wiley & Son, Inc., 1991.

Carbamation of the 6-O-Position

General methods of introducing the carbamate to the macrolide proceed with various reagents and conditions. Representative syntheses for attaching the carbamate to the C6-hydroxy are illustrated below in Scheme 1.

Scheme 1

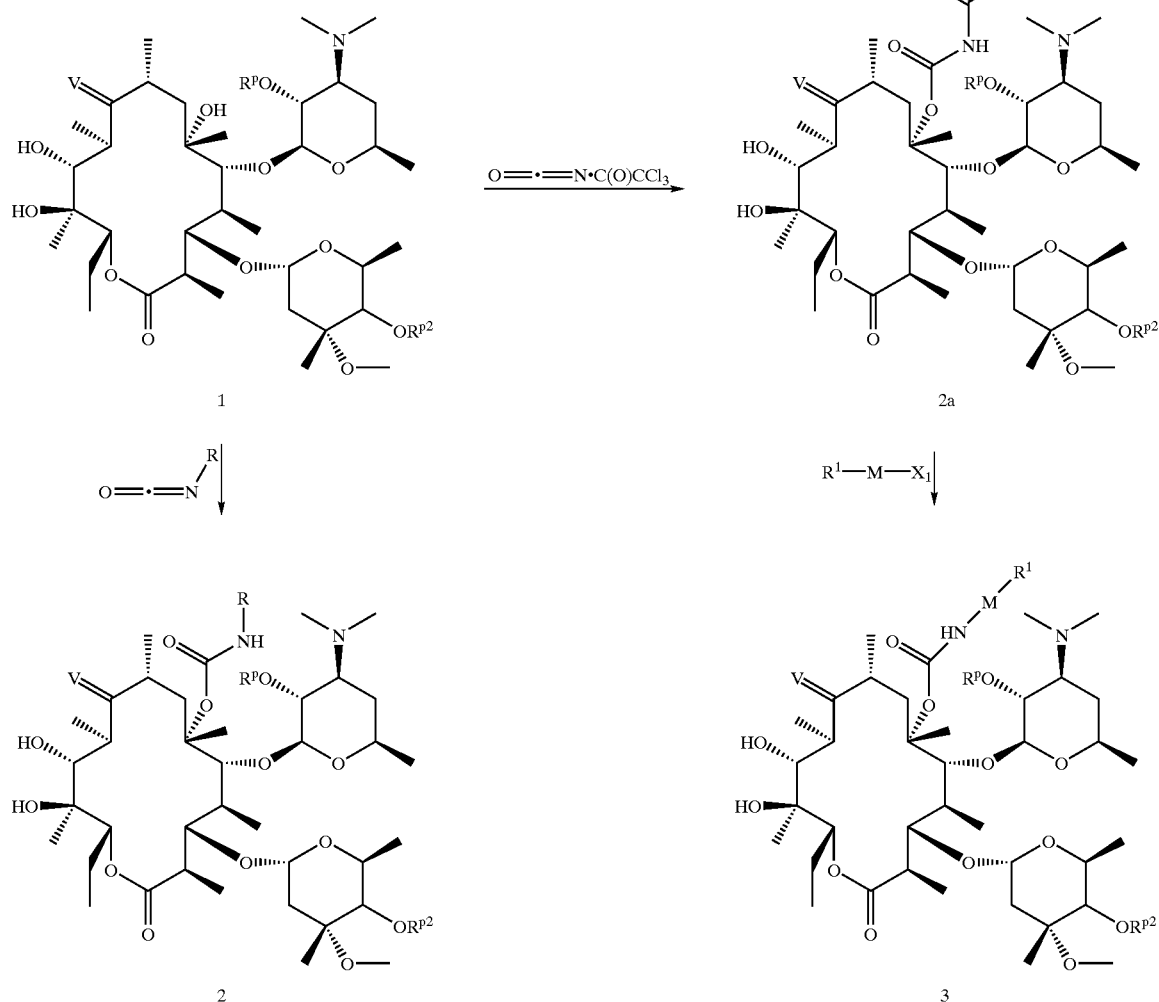

The introduction of the carbamate to the macrolide at 6-O-hydroxy can be accomplished by treating compound 1 with an isocyanate reagent in a polar or nonpolar aprotic solvent. Suitable isocyanate reagents include, but are not limited to, hydrocarbyl isocyanates, acyl isocyanates, and arylacyl isocyanates. For the sake of convenience, the isocyanate reagents are referred to by the general formula O=C=N—R, wherein R is a hydrocarbyl, hydrocarbylcarbonyl, or a hydrocarbylsulphonyl. In a preferred reagent, R denotes a group of the formula —M—R$^1$, —M—R$^2$, —C(O)—M—R$^1$, —C(O)—M—R$^2$, —SO$_2$—M—R$^1$, —SO$_2$—M—R$^2$, wherein M is an alkyl, alkenyl, or alkynyl group of the formulas —(CH$_2$)$_l$—, —(CH$_2$)$_m$—CH=CH—, and —(CH$_2$)$_n$—C≡C—, respectively, wherein 1 is 0 to 5, m is 0 to 3, and n is 0 to 3; R$^1$ is selected from hydrogen, aryl, substituted aryl, heteroaryl, substituted heteroaryl, and a group Ar$_1$—Ar$_2$, wherein Ar$_1$ and Ar$_2$ are independently selected from aryl, substituted aryl, heteroaryl, and substituted heteroaryl; and R$^2$ is independently selected from aryl, substituted aryl, heteroaryl, substituted heteroaryl, and Ar$_1$—Ar$_2$, wherein Ar$_1$ and Ar$_2$ are as previously defined. Representative reagents include, but are not limited to compounds of the formula O=C=N—M—R$^1$, O=C=N—M—R$^2$, O=C=N—C(O)—M—R$^1$, O=C=N—C(O)—M—R$^2$, O=C=N—SO$_2$—M—R$^1$, or O=C=N—SO$_2$—M—R$^2$, or an isocyanate of an acyl derivative. The reaction can be accomplished at 0° C. and gradually warmed up to room temperature or can be heated to reflux from 1–48 hours. Exemplary aprotic solvents suitable for the reaction include, but are not limited to, tetrahydrofuran, dimethyl sulfoxide, toluene, dioxane, dimethyl formamide, methylene chloride, and the like, or combination of the above solvents, such as tetrahydrofuran and dimethyl sulfoxide. Additionally, CuCl (0.05 to 1 eq.) can be optionally added.

An exemplary method of introducing the carbamate to the C6-hydroxy involves using a hydrocarbyl, acyl, or arylacyl isocyanate reagent. To compound 1 in an aprotic solvent, such as THF, at –10° C. to 40° C. is added the isocyanate reagent, for example allyl isocyanate (1–4 eq.), wherein R is an allyl moiety. CuCl (0.05–1 eq.) is added to the mixture. The reaction mixture is stirred at room temperature to 40° C. overnight. The reaction mixture was taken up in ethyl acetate and washed with NaHCO$_3$ and brine to give the 6-O-carbamate derivative 2 wherein R is the group defined above.

According to another exemplary method, an activated isocyanate is introduced to the C6-position of the erythromycin 1 followed by alkylation with an appropriate electrophile. Reacting compound 1 with the activated isocyanate under reaction conditions similar to those previously described above can give a corresponding 6-O-carbamate 2a, from which the activating group can be optionally removed. The carbamate 2a, or its derivatives wherein the activating group is already removed, can be reacted with a compound of the formula R$^1$—M—X$_1$, wherein R$^1$ and M are as previously defined and X$_1$ is a halide or a suitable leaving group, for example acetate, tosylate, or mesylate. Exemplary activated isocyanate reagents for the reaction include, but are not limited to acyl isocyanates, sulphonyl isocyanates, and the like. A preferred isocyanate for the reaction is trichloroacetyl isocyanate. Suitable bases include, but are not limited to, potassium t-butoxide, sodium hydride, sodium hydroxide, potassium hydroxide, and the like, or a combination thereof. The reaction is carried out in an aprotic solvent, as described above, to introduce the group —M—R$^1$ to the attached carbamate represented by 3.

Substituting R$^2$ for R$^1$ in R$^1$—M—X$_1$, in the above process provides the compound 3 wherein R$^1$ is R$^2$, and wherein R$^2$ is as previously defined.

Scheme 2

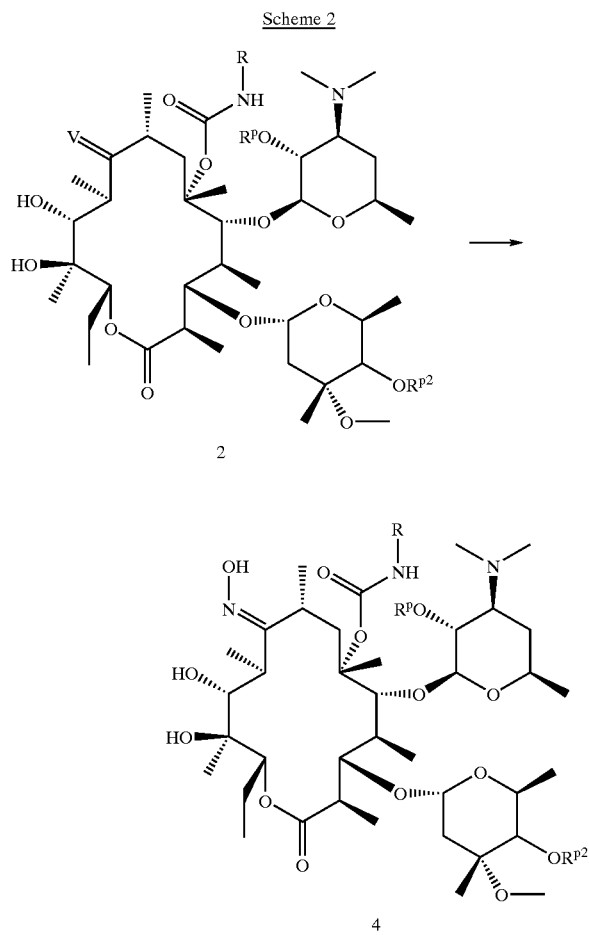

Deprotection of the C9-oxime of compound 2 or 3, wherein V is a protected oxime, is accomplished under neutral, acidic or basic conditions. Exemplary conditions for deprotecting a protected oxime of the formula N—O—C(O)—(CH$_2$)$_s$—R$^x$ include, but are not limited to, treatment with an alcoholic solvent at room temperature or at reflux. Preferably, the 9-oxime is deprotected in this manner when R$^p$ is an ester, such as acetate or benzoate. Alcoholic solvents preferred for the deprotection are methanol or ethanol. Exemplary conditions for converting the protected oxime N—O—C(R$^y$)(R$^z$)—R$^x$, wherein R$^x$, R$^y$, and R$^z$ are as defined above, to the oxime (N—OH) involve treating compound 2 or 3 with aqueous acid in acetonitrile. Aqueous acids suitable for the reaction include, but are not limited to, aqueous acetic acid, hydrochloric acid, and sulfuric acid. During the deprotection of the oxime, the 2'- and 4"-hydroxy protecting groups (R$^p$ and R$^{p2}$) can be removed in process. A thorough discussion of the procedures, reagents and conditions for removing protecting groups is discussed by T. W. Greene and P. G. M. Wuts in *Protective Groups in Organic Synthesis*, 2nd ed., John Wiley & Son, Inc., (1991), which is herein incorporated by reference.

Scheme 3

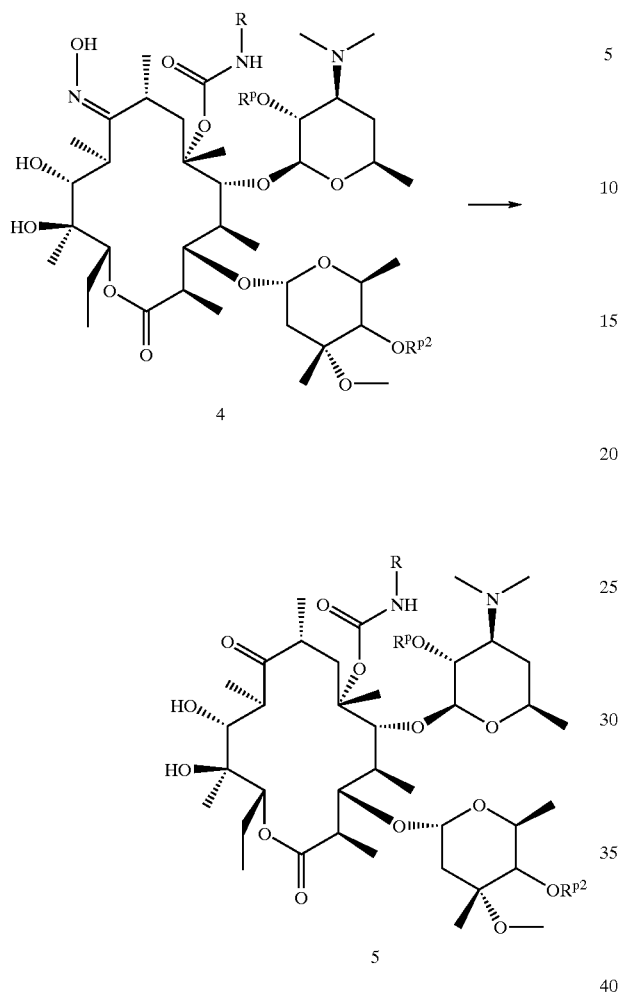

Scheme 4

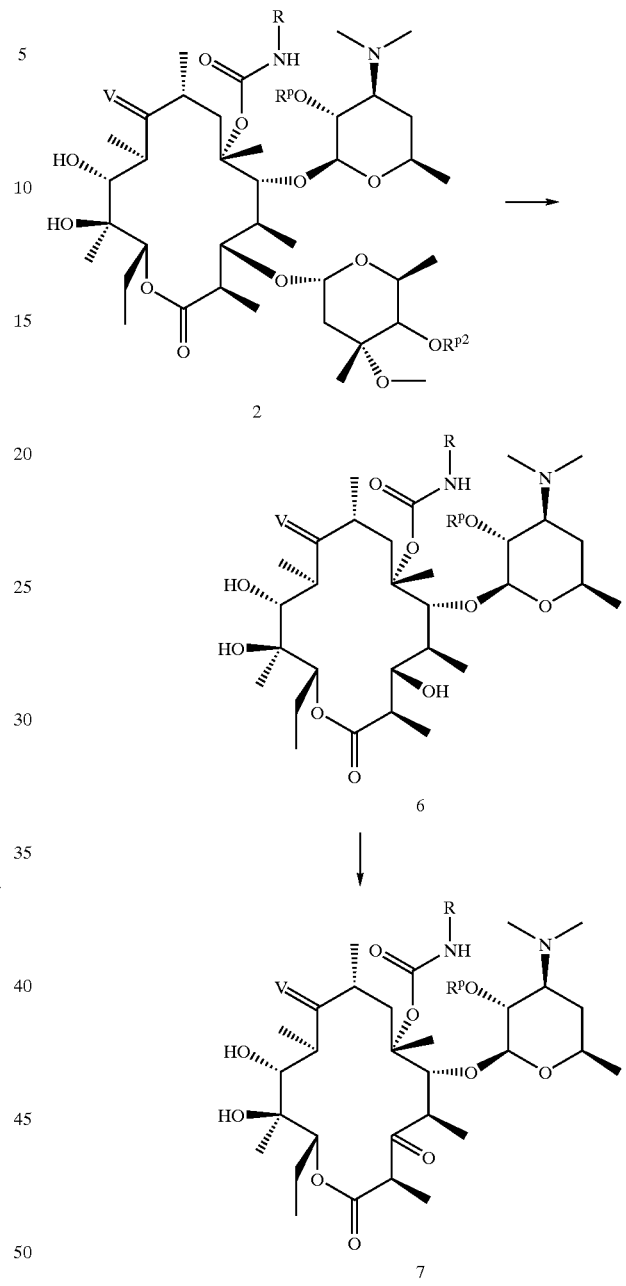

As shown in Scheme 3, the deoximation reaction can be carried out by reacting the C-9 oxime, with an inorganic sulfur oxide or an inorganic nitrite salt in a protic solvent. Exemplary inorganic sulfur oxide compounds are sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite, and the like. Suitable inorganic nitrite salts include, for example, sodium nitrite or potassium nitrite, and the like. Examples of the solvents used are protic solvents such as water, methanol, ethanol, propanol, isopropanol, trimethylsilanol, or a mixture of one or more of the mentioned solvents, and the like. The reaction is optionally carried out in the presence of an organic acid, such as formic acid, acetic acid and trifluoroacetic acid. Hydrochloric acid is also suitable for the reaction. The amount of acid used is from about 1 to about 10 equivalents of the amount of compound 4. In a preferred embodiment, the reaction of compound 4 is carried out using sodium nitrite and HCl in ethanol and water to give compound 5.

The cladinose moiety of compound 2 or 5 is removed by mild aqueous acid hydrolysis to give 6. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably −10° C. to 70° C.

The 2'-hydroxy group of the macrolide is optionally protected as previously described using a hydroxy protecting reagent in an aprotic solvent. Preferred hydroxy protecting reagents are acetic anhydride, benzoyl anhydride, benzyl chloroformate or trialkylsilyl chloride. Preferably, the aprotic solvent is dichloromethane, chloroform, DMF, tetrahydrofuran (THF), N-methyl pyrrolidinone or a mixture thereof. A particularly preferred protecting group $R^p$ is acetate or benzoate. Protection of the hydroxy group can be accomplished before or after the descladinozation reaction.

The 3-hydroxy group of 6 is oxidized to the ketone 7 using a modified Swern oxidation procedure or Corey-Kim oxidation conditions. Suitable oxidizing agents are N-chloro-succinimide-dimethyl sulfide or carbodiimide-dimethylsulfoxide. In a typical example, 6 is added into a pre-formed N-chlorosuccinimide and dimethyl sulfide complex in a chlorinated solvent, such as methylene chloride, at −10 to 25° C. After stirring for 0.5–4 hours, a tertiary amine, such as triethylamine or Hunig's base, is added to produce the corresponding ketone.

Preparation of 11 12-Carbamate Derivatives

Compound 2 or 7 can be further treated to obtain 11,12-carbamate compounds of formula (II), (II-A), (IV), (IV-A), (IV), and (VI-A) and the tricyclic imine derivatives of formula (I), (III), and (V), as illustrated below in Schemes 5 and 6. In the case of compound 2, cleavage of the cladinose sugar and oxidation of the 3-hydroxy to a 3-keto group can be accomplished after 11,12-carbamate formation.

Scheme 5

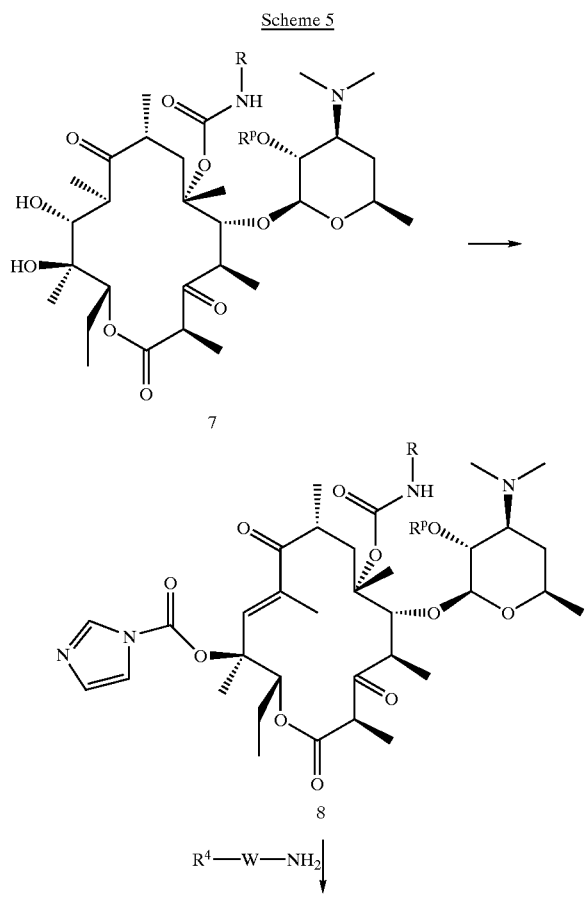

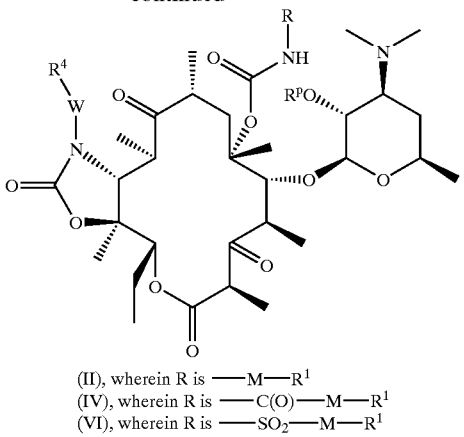

(II), wherein R is ——M——$R^1$
(IV), wherein R is ——C(O)——M——$R^1$
(VI), wherein R is ——$SO_2$——M——$R^1$ According to Scheme 5, intermediate compound 8 may be prepared from compound 7, by treatment of the latter under anhydrous conditions with an alkali metal hydride or bis(trimethylsilyl) amide in the presence of carbonyldiimidazole in an aprotic solvent. The aprotic solvent can be selected from the group as previously defined. Exemplary reagents can be selected from sodium hydride, lithium hydride, sodium hexamethyldisilazide, and lithium hexamethyldisilazide. Preferably, the solvent is tetrahydrofuran, dimethylformamide, or a mixture thereof. The reaction may require cooling or heating, depending upon the conditions used. The reaction temperature may be from −20° C. to 70° C., and preferably from 0° C. to room temperature. The reaction may require 0.5 hours to 10 days, and is preferably accomplished in 1 to 5 days.

Alternatively, compound 7 is treated with an alkali metal hydride and a phosgene reagent under anhydrous conditions, followed by a base catalyzed decarboxylation, or can be treated with methanesulfonic anhydride in pyridine, followed by treatment with an amine base to provide a suitable intermediate for treatment with the alkali metal hydride base and carbonyldiimidazole to give compound 8 in a stepwise manner. Preferably, the phosgene reagent is phosgene, diphosgene, or triphosgene.

Compound 8 is reacted with a primary amine $R^4$—W—$NH_2$, wherein $R^4$ and W are as previously defined. The reaction is carried out in a suitable solvent from room temperature to reflux temperature for about 4 to about 48 hours. Exemplary solvents are acetonitrile, tetrahydrofuran, dimethyl formamide, dimethylsulfoxide, dimethyl ether, N-methyl pyrrolidinone, water, or a mixture thereof. Preferred solvents are aqueous acetonitrile, and aqueous DMF.

The prepared 11,12-carbamate derivatives are optionally deprotected and a compound of formula (II), (IV), and (VI) can be isolated. When the protecting group $R^p$ or $R^{p2}$ is an ester, the protecting group may be removed by treatment with an organic alcohol, such as methanol or ethanol. Exemplary esters which can be deprotected by treating the ketolide derivatives with an organic alcohol are acetate, benzoate, and the like. When the protecting group is a trialkylsilyl group, deprotection by treatment with fluoride in a polar organic solvent, such as THF or acetonitrile, or aqueous acid hydrolysis is preferred.

To obtain derivatives of formula (II-A), (IV-A), and (VI-A), wherein A in the structural formula corresponds to —NH—, compound 8 is reacted with aqueous ammonia hydroxide or anhydrous ammonia, preferably in acetonitrile, under the conditions as described above for the primary amine optionally followed by the deprotection of the 2' hydroxy protecting group as described above.

Scheme 6

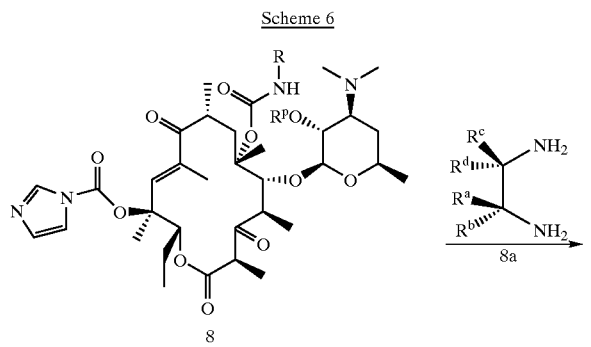

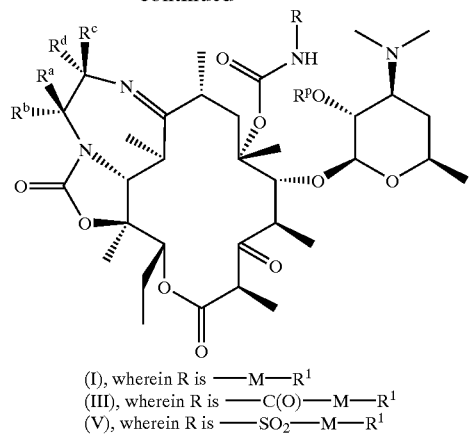

(I), wherein R is ——M——R¹
(III), wherein R is ——C(O)——M——R¹
(V), wherein R is ——SO₂——M——R¹

As illustrated above in Scheme 6, compound 8 can be reacted with a diamine compound 8a, wherein $R^a$, $R^b$, $R^c$ and $R^d$ are as previously defined, in a suitable polar organic solvent to obtain a corresponding bicyclic amine compound 9. Exemplary solvents for the reaction are selected from the group consisting of aqueous acetonitrile, DMF, aqueous DMF, and the like. One amino group of the diamine reagent can be optionally protected to differentiate the two diamine and deprotected prior to cyclization.

Cyclization of the bicyclic amine 9 by treatment with dilute acid in a suitable organic solvent affords the tricyclic derivatives of the invention. The reaction can be accomplished in a period of from about 1 to 10 days at temperatures from about room temperature to reflux. Exemplary acids are acetic acid or HCl. A suitable organic solvent is selected from alcoholic solvents, such as methanol, ethanol, propanol, and the like, or non polar solvent, such as benzene or toluene.

Optional deprotection of the compound obtained therefrom affords a tricyclic ketolide derivative of Formula (I), (III), and (V).

Preparation of 11,12-Carbonate Compounds

Carbonate-type derivatives of the invention are compounds represented by the general formula (II-A), (IV-A), and (VI-A), wherein A in the structural formula represents an oxygen heteroatom. A representative method for preparing carbonate compounds of the invention follows below in Scheme 7.

Scheme 7

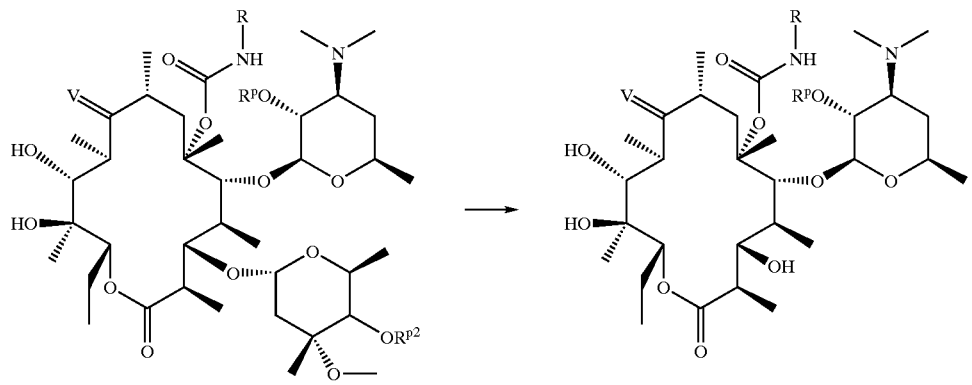

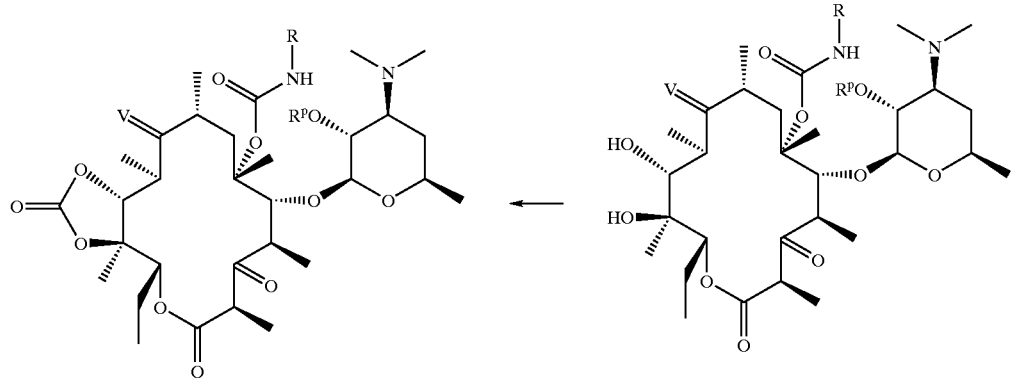

11

(II-A), wherein R is —M—$R^2$
(IV-A), wherein R is —C(O)—M—$R^2$
(VI-A), wherein R is —$SO_2$—M—$R^2$ An intermediate 10 can be obtained by removing the cladinose group of compound 2 or 3. Oxidizing the 3-hydroxy of compound 10 provides compound 11. Compound 11 is converted to a cyclic carbonate compound of formula (II-A), (IV-A), and (VI-A), wherein A is —O—, by reaction with carbonyldiimidazole and sodium hexamethyldisilazide or by reacting with triphosgene in pyridine. A summary of methods for the preparing the cyclic carbonate is described by Baker et al., *J. Org. Chem.*, 1988, 53, 2340. The 2'-hydroxy of the cyclic carbonate can be optionally deprotected by methods as previously described.

Another method of preparing an 11,12-carbonate erythromycin derivative involves treatment of compound 1, preferably as the protected or deprotected oxime, with excess isocyanate reagent and optionally alkylating under the conditions as previously described for Scheme 1. The reaction provides an 11,12-carbonate derivative 13 having a 6-O-carbamate group optionally substituted on the nitrogen atom, as illustrated in Scheme 8 below.

Scheme 8

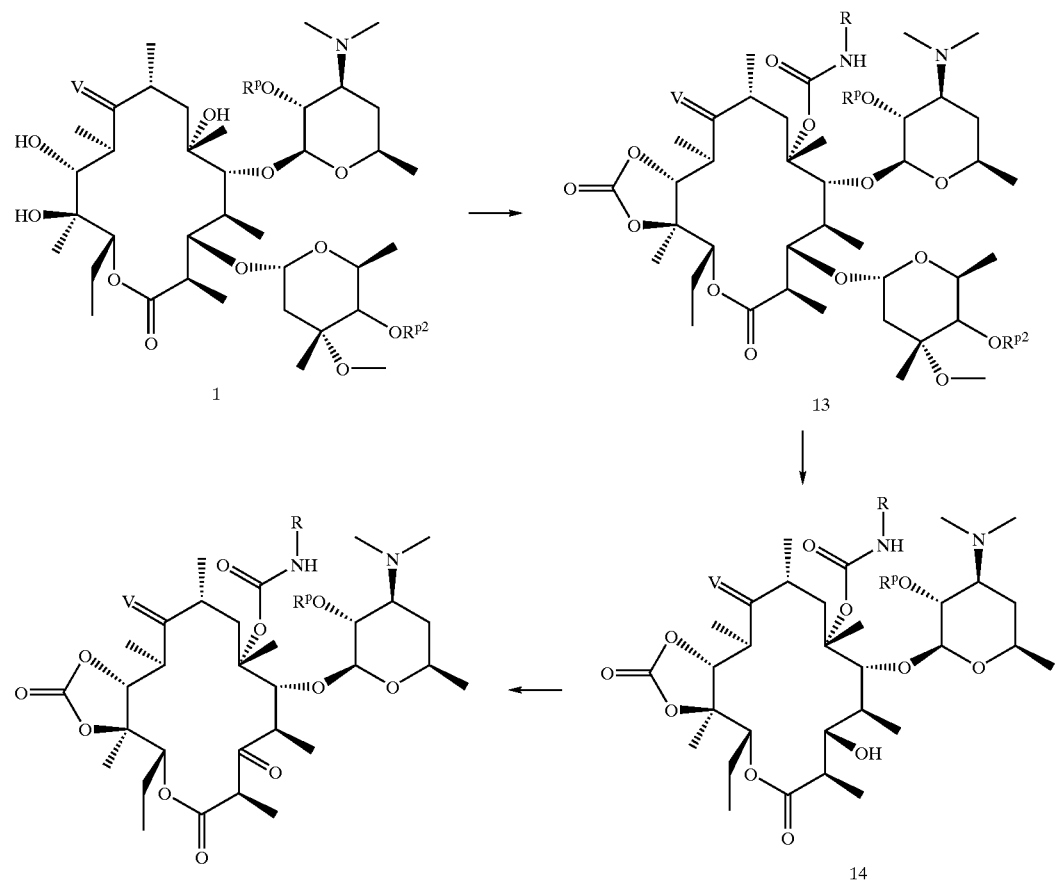

(II-A), wherein R is —M—R²
(IV-A), wherein R is —C(O)—M—R²
(VI-A), wherein R is —SO₂—M—R²
Compound 13 provides a useful derivative from which the cladinose group can be optionally removed under hydrolysis conditions and the 3-hydroxy oxidized under reaction conditions as similar to those described for Scheme 4.

Coupling of an Aromatic Group

6-O-allyl- and 6-O-propargyl-substituted 11,12-diol, 11,12-carbamate, and tricyclic ketolide derivatives of erythromycin can be optionally coupled with an aromatic group to obtain compounds of formula I, II, II-A, III, IV, IV-A, V, VI, and VI-A, wherein R¹ or R² is aryl, substituted aryl, heteroaryl, substituted heteroaryl, heterocycloalkyl, substituted heterocycloalkyl, or Ar₁—Ar₂, wherein Ar₁ and Ar₂ are as previously defined.

A compound having 6-O-substitution

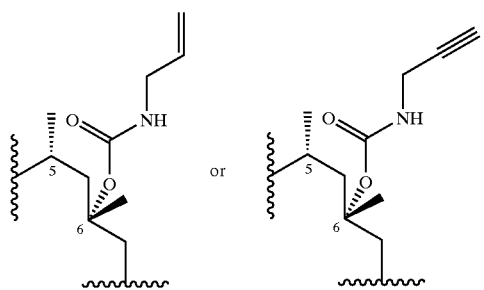

can be coupled with a suitable aromatic group by methods of transition metal-catalyzed coupling. Methods for coupling aryl groups to the 6-O-allyl and 6-O-propargyl groups of macrolide derivatives are described in U.S. Pat. No. 5,866,549 and U.S. patent application Ser. No. 08/940,871, which are herein incorporated by reference.

A suitable aromatic group can be provided by an aromatic halide or aromatic trifluoromethanesulfonate reagent. Examples of such reagents include, but are not limited to, an aryl halide, substituted aryl halide, heteroaryl halide, or substituted heteroaryl halide, or a bifunctionalized aryl or heteroaryl precursor group.

Reaction of the allyl-substituted derivatives with an aryl halide is performed in the presence of Pd(II) or Pd(0) catalysts with promoters such as phosphines, arsines, amines, and inorganic bases in polar, aprotic solvents; see Organic Reactions, 1982, 27, 345–390. Preferably, the promoters are selected from triphenylphosphine, triphenylarsine, pyridine and triethylamine, potassium carbonate, and cesium fluoride. The aprotic solvents are as previously defined such as dimethylformamide, dimethyl sulfoxide, dimethylethane, acetonitrile, tetrahydrofuran, or mixtures thereof. The reaction is accomplished at temperatures from about room temperature to about 1 50° C., depending on the reagents chosen and the nature of the aryl halide.

The 6-O-propargyl groups can be derivatized under Sonagashira conditions by combining the alkyne derivative with an aryl halide in the presence of a phosphine promoter and Cu(I) optionally in the presence of an organic base. Preferably, the organic base is triethylamine. Summary of the procedures, reagents, and solvents for coupling terminal alkynes with aryl halides is described in Tetrahedron Lett., 1975, 50, 4467–4470.

The propargyl carbamate derivatives can be derivatized with borane-THF in aprotic solvents at temperatures from about −20° C. to about room temperature to provide vinyl boronic acid derivatives. The vinyl boronic acid derivatives can be reacted under Suzuki conditions with aryl halide reagents, catalysts and promoters to provide allyl products similar to the Heck coupling reaction of the aryl halide as described above. A thorough discussion of Suzuki conditions is provided in Chemical Reviews, 1995, Vol. 95, No. 7,2457–2483.

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the innoculum spot as compared to the growth control. The results of this assay, which relate to the antibacterial activity of the compounds of the invention, are reported below in Table 1.

TABLE 1

MIC's of Selected Compounds

| Microorganism | Ery. A standard | Ex. 1 | Ex. 2 |
|---|---|---|---|
| Staphylococcus aureus ATCC 6538P | 0.2 | 0.39 | 1.56 |
| Staphylococcus aureus A5177 | 3.1 | 0.39 | 3.1 |
| Staphylococcus aureus A-5278 | >100 | >100 | >100 |
| Staphylococcus aureus CMX 642A | 0.39 | — | — |
| Staphylococcus aureus NCTC10649M | 0.39 | 0.39 | 1.56 |
| Staphylococcus aureus CMX 553 | 0.39 | — | — |
| Staphylococcus aureus 1775 | >100 | >100 | >100 |
| Staphylococcus epidermidis 3519 | 0.39 | 0.39 | 1.56 |
| Streptococcus bovis A-5169 | 0.02 | 0.02 | 0.2 |
| Streptococcus agalactiae CMX 508 | 0.05 | 0.02 | 0.39 |
| Streptococcus pyogenes EES61 | 0.05 | 0.02 | 0.39 |
| Streptococcus pyogenes 930 | >100 | >100 | >100 |
| Streptococcus pyogenes PIU 2548 | 6.2 | 1.56 | 3.1 |
| Micrococcus luteus ATCC 9341 | 0.05 | — | — |
| Micrococcus luteus ATCC 4698 | 0.2 | 0.39 | 1.56 |
| Escherichia coli JUHL | >100 | 50 | >100 |
| Escherichia coli SS | 0.78 | 0.39 | 1.56 |
| Escherichia coli DC-2 | >100 | 100 | >100 |
| Candida albicans CCH 442 | >100 | >100 | >100 |
| Mycobacterium smegmatis ATCC 114 | 3.1 | 50 | 50 |
| Nocardia asteroides ATCC997O | 0.1 | 0.78 | 6.2 |

In a separate assay representative compounds of the invention were assayed in vitro for antibacterial activity against H. Influenza Dill AMP R strain and S. Pneumonia, according to the protocol described above. The results of this assay, which relate to the antibacterial activity of compounds of the invention against the H. Influenza Dill AMP R and S. Pneumonia organisms, are shown below in Table 2.

TABLE 2

| Microorganism | Ery. A standard | Ex. 1 | Ex. 2 |
| --- | --- | --- | --- |
| *Haemophilis influenzae* DILL AMP R | 4 | 8 | 8 |
| *Streptococcus pneumonia* ATCC6303 | 0.06 | 0.03 | 0.25 |
| *Streptococcus pneumonia* GYR 1171 | 0.06 | 0.03 | 0.25 |
| *Streptococcus pneumonia* 5649 | 16 | 2 | 8 |
| *Streptococcus pneumonia* 5979 | >128 | >64 | >128 |

The compounds and processes of the invention will be better understood in connection with the following examples, which are intended as an illustration of and not a limitation upon the scope of the invention as defined in the appended claims.

EXAMPLES

Example 1

Compound of Formula (IV-A): wherein A is —O—; X is N—OH; —M— is Absent, $R^2$ is Phenyl; and $R^p$ is Hydrogen Step 1(a): Compound 13 from Scheme 8, wherein V is N—O-(1-Isopropoxycyclohexyl); R is —C(O)—M—$R^2$, wherein —M— is Absent and $R^2$ is Phenyl; $R^p$ is Benzoyl; and $R^{p2}$ is Benzoyl.

To compound 2',4"-bis-O-benzylerythromycin A 9-[O-(1-isopropoxycyclohexyl)oxime] (2 g, 1.82 mmol) in 5 ml of $CH_2Cl_2$ at 0° C. was added benzoyl isocyanate ($CH_2Cl_2$ solution, c=1 mg/ml, 0.402 ml, 402 mg, 2.73 mmol) dropwise. The reaction was allowed to warm up to RT slowly and stirred at RT over night. Another 2.73 mmol of benzoyl isocyanate solution was added and the reaction mixture was stirred for another 24 hours. MeOH was added to quench the excess isocyanate and the mixture was evaporated to dryness under vacuum. Column chromatography with 10–20% acetone/hexanes provided the title compound.

HRMS(m/e) Cal'd for $C_{69}H_{96}N_3O_{19}$ (M+H)=1270.6633, Observed=1270.6628. $^{13}C$ NMR(100 MHz, $CDCl_3$): δ 175.9, 166.0, 165.5, 165.1, 164.4, 153.5, 148.3, 133.2, 132.7, 132.7, 132.6, 130.8, 129.6, 129.5, 128.7, 128.7, 128.4, 128.2, 127.9, 104.6, 99.2, 95.3, 87.4, 85.2, 81.7, 78.4, 77.8, 77.4, 75.1, 73.3, 72.7, 67.6, 64.8, 63.3, 63.1, 49.4, 45.5, 40.8, 38.9, 35.8, 35.5, 35.1, 33.4, 32.9, 31.6, 25.9, 25.4, 24.4, 24.3, 22.9, 22.9, 21.8, 21.8, 21.4, 21.0, 18.7, 17.5, 16.3, 15.1, 12.4, 10.2, 9.5.

Step 1(b): Compound 14 from Scheme 8, wherein V is N—OH; R is —C(O)—M—$R^2$, wherein —M— is Absent and $R^2$ is Phenyl; and $R^p$ is Benzoyl.

To a solution of the compound from step 1(a) (1.0 g, 0.79 mmol) in ethanol (50 ml) was added 50 ml of 2N HCl at 25° C. The mixture was heated up to 50° C. for four hours then over night at RT. The mixture was neutralized to pH 8~9 with sodium carbonate and was taken up in ethyl acetate (50 ml) and washed with saturated $NaHCO_3$, brine, and dried over $Na_2SO_4$. Removal of the solvents provided the title compound.

MS m/e (M+H)=868.

Step 1(c): Compound 14 from Scheme 8, wherein V is N—OAc; R is —C(O)—M—$R^2$, wherein —M— is Absent and $R^2$ is Phenyl; and $R^p$ is Benzoyl.

To the solution of compound obtained from step 1(b) (860 mg, 1 mmol) in 5 ml of $CH_2Cl_2$ was added acetic anhydride (0.139 ml, 1.5 eq.) followed by $Et_3N$ (0.197 ml, 1.5 eq.) at 0° C. The reaction mixture was allowed to warm up to RT and stirred over night. The mixture was taken up with 200 ml of ethyl acetate, the organic layer was washed with $NaHCO_3$, brine, and dried over $Na_2SO_4$. Removal of the solvents and column chromatography with 20% acetone/hexanes provided the title compound. MS m/e (M+H)=910.

Step 1(d): Compound of Formula (IV-A), wherein A is —O—; X is N—OAc; —M— is Absent; $R^2$ is Phenyl; and $R^p$ is Benzoyl.

To the solution of NCS (131 mg, 2 eq.) in 4 ml of $CH_2Cl_2$ at −10° C. was added $Me_2S$ (0.071 ml, 2 eq.) dropwise. White precipitate was formed. 30 minutes later the compound obtained from step 1(c) (450 mg, 0.495 mmol, 1 eq.) in 2 ml of $CH_2Cl_2$ was added slowly to the mixture over a ten minutes period. The mixture was stirred for 40 minutes at −10° C. and $Et_3N$ was added. The mixture was taken up with 200 ml of ethyl acetate, the organic layer was washed with $NaHCO_3$, brine, and dried over $Na_2SO_4$. Removal of the solvents and column chromatography with 20% acetone/hexanes gave the title compound.

MS m/e (M+H)=908.

Step 1(e): Compound of Formula (IV-A), wherein A is —O—, X is N—OH; —M— is Absent; $R^2$ is Phenyl; and $R^p$ is Hydrogen.

The title compound was obtained by refluxing the compound obtained in step 1(d) in methanol followed by removal of the solvents and column chromatography with 3% MeOH/$CH_2Cl_2$.

HRMS(m/e) Cal'd for $C_{38}H_{55}N_3O_{13}$ (M+H)=762.3808, Observed=762.3807. $^{13}C$ NMR(100 MHz, $CDCl_3$): δ 203.9, 171.5, 167.6, 164.7, 153.3, 147.9, 132.8, 132.7, 128.8, 127.9,102.9, 86.2, 85.0, 82.4, 76.6, 76.2, 70.2, 69.4, 66.1, 50.8, 46.0, 40.2, 37.0, 33.3, 28.7, 25.3, 21.9, 21.2, 21.1, 18.6, 15.3, 15.2, 13.0, 12.7, 10.0.

Example 2

Compound of Formula (II-A), wherein A is —O—; X is N—OH; —M— is Absent; $R^2$ is Hydrogen, and $R^p$ is Hydrogen Step 2(a): Compound 13 from Scheme 8, wherein V is N—O-(1-Isopropoxycyclohexyl); R is —C(O)$CCl_3$; $R^p$ is Benzoyl; and $R^{p2}$ is Benzoyl.

To compound 2',4"-bis-O-benzylerythromycin A 9-[O-(1-isopropoxycyclohexyl)oxime] (10.5 g, 9.6 mmol) in 20 ml of $CH_2Cl_2$ at 0° C. was added trichloroacetyl isocyanate (3.4 ml, 5.4g, 3 eq.) dropwise. The reaction was allowed to warm up to RT slowly and stirred at RT for 56 hours. MeOH was added to quench the excess isocyanate and the mixture was evaporated to dryness under vacuum. Column chromatography with 10–20% acetone/hexanes provided the title compound.

MS m/e (M+H)=1310.

Step 2(b): Compound 14 from Scheme 8, wherein V is N—OH; R is —M—$R^2$, wherein —M— is Absent and $R^2$ is Hydrogen; and $R^p$ is Benzoyl.

To a solution of compound obtained from step 2(a) (1.7 g, 1.2 mmol) in ethanol (50 ml) was added 50 ml of 2N HCl at 25° C. The mixture was heated up to 50° C. for four hours then over night at RT. The mixture was neutralized to pH 8~9 with sodium carbonate and was taken up in ethyl acetate (50 ml) and washed with saturated $NaHCO_3$, brine, and dried over $Na_2SO_4$. Removal of the solvents gave the title compound.

MS m/e (M+H)=764.

Step 2(c): Compound 14 from Scheme 8, wherein V is N—OAc; R is —M—$R^2$, wherein —M— is Absent and $R^2$ is Hydrogen; and $R^p$ is Benzoyl.

To the solution of the compound obtained in step 2(b) (1.4 g, 1.83 mmol ) in 5 ml of $CH_2Cl_2$ was added acetic anhydride (0.259 ml, 1.5 eq.) followed by Et$_3$N (0.393 ml, 1.5 eq.) at 0° C. The reaction mixture was allowed to warm up to RT and stirred over night. The mixture was taken up with 200 ml of ethyl acetate, the organic layer was washed with NaHCO$_3$, brine, and dried over Na$_2$SO$_4$. Removal of the solvents and column chromatography with 20% acetone/hexanes gave the title compound.

MS m/e (M+H)=806.

Step 2(d): Compound of Formula (II-A), wherein A is —O—; X is N—OAc; —M— is Absent; R$^2$ is hydrogen: and R$^p$ is Benzoyl.

To the solution of NCS (244 mg, 1.7 eq.) in 10 ml of CH$_2$Cl$_2$ at −10° C. was added Me$_2$S (0.198 ml, 2.5 eq.) dropwise. White precipitate was formed. Thirty minutes later the compound obtained from step 2(c) (870 mg, 1.08 mmol, 1 eq.) in 2 ml of CH$_2$Cl$_2$ was added slowly to the mixture over a 15 minutes period. The mixture was stirred for 40 minutes at −10° C. and Et$_3$N was added. The mixture was taken up with 200 ml of ethyl acetate, the organic layer was washed with NaHCO$_3$, brine, and dried over Na$_2$SO$_4$. Removal of the solvents and column chromatography with 10~25% acetone/hexanes gave the title compound.

MS m/e (M+H)=804.

Step 2(e): Compound of Formula (II-A), wherein A is —O—; X is N—OH; —M— is Absent; R$^2$ is Hydrogen; and R$^p$ is Hydrogen.

The title compound was obtained by refluxing compound obtained from step 2(d) in methanol followed by removal of the solvents and column chromatography with 50% acetone/hexanes.

HRMS(m/e) Cal'd for C$_{31}$H$_{51}$N$_3$O$_{13}$ (M+H)=658.3551, Observed=658.3557. $^{13}$C NMR(100 MHz, CDCl$_3$): δ 204.9, 170.9, 166.0, 155.1, 153.6, 103.0, 84.9, 83.7, 82.7, 77.6, 76.5, 70.3, 69.3, 65.9, 50.8, 45.2, 40.1, 37.1, 32.8, 28.4, 25.2, 22.2, 21.1, 20.7, 18.8, 15.5, 15.3, 12.7, 12.6, 10.2.

Example 3

Compound of Formula (II-A): wherein A is —O—; X is N—OH; —M— is —CH$_2$—CH=CH— and R$^1$ is 3-guinolyl; and R$^p$ is Hydrogen Step 3(a): Compound 13 from Scheme 8, wherein V is N—O-(1-Isopropoxycyclohexyl); R is —M—R$^1$, wherein —M— is —CH$_2$—CH=CH— and R$^1$ is Hydrogen: R$^p$ is H; and R$^{p2}$ is Benzoyl.

To a compound obtained from example 2, step 2(a), (1.0 g, 0.76 mmol) in MeOH (50 ml) was added water (25 ml) and triethylamine (2 ml). The mixture was heated at reflux for 2 hours and at room temperature over night. The solvents were removed and the residue was dissolved in ethyl acetate (400 ml) and washed with aqueous NaHCO$_3$, brine, and dried (Na$_2$SO$_4$). Removal of the solvent gave the title compound as a crude product which was used as is in step 3(b).

MS m/e (M+H)=1062 .

Step 3(b): Compound 13 from Scheme 8, wherein V is N—O-(1-Isopropoxycyclohexyl); R is —M—R$^1$, wherein —M— is —CH$_2$—CH=CH— and R$^1$ is Hydrogen; R$^p$ is Benzoyl; and R$^{p2}$ is Benzoyl.

To the crude product from step 3(a) (806 mg, 0.76 mmol) in CH$_2$Cl$_2$ (15 ml) at 0° C. was added benzoic anhydride (382 mg, 1.52 mmol) and triethyl amine (0.317 ml, 2.28 mmol). The mixture was stirred at room temperature for 24 hours and diluted with ethyl acetate and washed with aqueous NaHCO$_3$, brine, and dried (Na$_2$SO$_4$). Removal of the solvent and column chromatography on 10 g silica gel with 25% EtOAc/hexanes gave the title compound (800 mg).

MS m/e (M+H)=1166.

Step 3(c): Compound 13 from Scheme 8, wherein V is N—O—(1-Isopropoxycyclohexyl); R is —M—R$^1$, wherein —M— is —CH$_2$—CH=CH— and R$^1$ is Hydrogen; R$^p$ is Benzoyl; and R$^{p2}$ is Benzoyl.

To a compound from step 3(b) (960 mg, 0.823 mmol), diphenyl phosphino butane (4.2 mg, 0.0098 mmol), Pd$_2$(dba)$_3$ (4.5 mg, 0.0049 mmol), and t-butyl allyl carbonate (195 mg, 1.23 mmol) in a flamed-dry flask was charged with dried tetrahydrofurane (3 ml) and was degassed. The mixture was stirred at room temperature for 10 minutes then heated to reflux for 3 hours. Removal of the solvent and column chromatography on silica gel with 5% acetone/hexanes then 10% acetone/hexanes gave the title compound (750 mg).

MS m/e (M+H)=1206.

Step 3(d): Compound 13 from Scheme 8, wherein V is N—OH: R is —M—R$^1$, wherein —M— is —CH$_2$—CH=CH— and R$^1$ is Hydrogen; R$^p$ is Benzoyl; and R$^{p2}$ is Benzoyl.

To a compound from step 3(c) (710 mg, 0.588 mmol) in acetonitrile (8 ml) at room temperature was added acetic acid (3 ml) and water (4 ml) and stirred at room temperature for 24 hours then adjusted to pH~8–9 with triethylamine. The organic solvents were partially removed and diluted with ethyl acetate and washed with aqueous NaHCO$_3$, brine, and dried (Na$_2$SO$_4$). Removal of the solvent gave the title compound (500 mg).

MS m/e (M+H)=1066.

Step 3(e): Compound 13 from Scheme 8, wherein V is N—OH: R is —M—R$^1$, wherein —M— is —CH$_2$—CH=CH— and R$^1$ is 3-guinolyl; R$^p$ is Benzoyl; and R$^{p2}$ is Benzoyl.

A slurry of the product from step 3(d) (500 mg, 0.47 mmol), 3-bromoquinoline (194 mg, 0.94 mmol), Pd(OAc)$_2$ (31 mg, 0.141 mmol), tri-o-tolylphosphine (86 mg, 0.282 mmol), and triethylamine (0.163 ml) in degassed acetonitrile (5 mL) was heated at 90° C. in a sealed vessel for 72 hours. The reaction mixture was diluted with ethyl acetate and washed with 5% aqueous NaHCO$_3$, brine, and dried (Na$_2$SO$_4$). Removal of the solvent and column chromatography with 40% EtOAc/hexanes then 25% acetone/hexanes gave the title compound (180 mg).

MS m/e (M+H)=1193.

Step 3(f): Compound 14 from Scheme 8, wherein V is N—OH: R is —M—R$^1$, wherein —M— is —CH$_2$—CH=CH— and R$^1$ is 3-quinolyl; and R$^p$ is Benzoyl.

A suspension of the product from step 3(e) in ethanol/water (1:2) is treated with 1N HCl (10 eq.), stirred at 50° C. for 6 hours then cooled to 0° C. and made basic to pH~9–10 with 2N NaOH. The mixture is concentrated to remove most of ethanol and extracted with ethyl acetate. The organics are washed with brine and dried (MgSO$_4$). Removal of the solvents and purification on silica gel column provides the title compound.

Step 3(g): Compound 14 from Scheme 8, wherein V is N—OAc; R is —M—R$^1$, wherein —M— is —CH$_2$—CH=CH— and R$^1$ is 3-quinolyl; and R$^p$ is Benzoyl.

To the solution of the compound obtained in step 3(f) (1 eq.) in CH$_2$Cl$_2$ is added acetic anhydride (1.5 eq.) followed by Et$_3$N (1.5 eq.) at 0° C. The reaction mixture is allowed to warm up to RT and stirred over night. The mixture is taken up with ethyl acetate, the organic layer is washed with NaHCO$_3$, brine, and dried over Na$_2$SO$_4$. Removal of the solvents and column chromatography with 20% acetone/hexanes gives the title compound.

Step 3(h): Compound of Formula (II-A): wherein A is —O—; X is N—OH; —M— is —CH$_2$—CH=CH—; R$^2$ is 3-guinolyl; and R$^p$ is Benzoyl.

To the solution of NCS (1.7 eq.) in $CH_2Cl_2$ at −10° C. is added $Me_2S$ (2.5 eq.) dropwise. White precipitate is formed. Thirty minutes later the compound obtained from step 3(g) (1 eq.) in of $CH_2Cl_2$ is added slowly to the mixture over a 15 minutes period. The mixture is stirred for 40 minutes at −10° C. and $Et_3N$ was added. The mixture is taken up with ethyl acetate and is washed with $NaHCO_3$, brine, and dried over $Na_2SO_4$. Removal of the solvents and column chromatography with 10~25% acetone/hexanes gives the title compound.

Step 3(i): Compound of Formula (II-A): wherein A is —O—; X is N—OH: —M— is —$CH_2$—CH=CH—; $R^2$ is 3-guinolyl; and $R^P$ is Hydrogen.

A solution of a compound from step 3(h) in methanol is heated at reflux for 4 hours. Removal of the solvent and column chromatography with 10% methanol/$CH_2Cl_2$ gives the title compound.

Example 4

Compound of Formula (II): wherein W is absent; $R^4$ is H; X is O; —M— is —$CH_2$—CH=CH—; $R^1$ is Hydrogen; and $R^P$ is Hydrogen Step 4(a): Compound 2 from Scheme 1 wherein V is N—O-(1-Isopropoxycyclohexyl); R is —M—$R^1$, wherein —M— is —$CH_2$-CH=CH— and $R^1$ is Hydrogen; $R^P$ is Benzoyl; and $R^{p2}$ is Benzoyl.

To compound 2',4"-bis-O-benzoyl erythromycin A 9-[O-(1-isopropoxycyclohexyl)-oxime] (200 mg, 0.182 mmol) in 1.5 ml THF at 0° C. was added allyl isocyanate (30 mg, 0.364 mmol) followed by CuCl (3 mg, 0.031 mmol). The reaction was allowed to warm up to RT slowly and stirred at RT over night. The mixture was taken up in ethyl acetate (200 ml) and washed with saturated $NaHCO_3$, brine, and dried over $Na_2SO_4$. Removal of the solvents and column chromatography with 20% ethyl acetate/hexanes provided the title compound.

MS m/e (M+H)=1180.

Step 4(b): Compound 4 from Scheme 2, wherein R is —M—$R^1$, wherein —M— is —$CH_2$—CH=CH— and $R^1$ is Hydrogen; $R^P$ is Benzoyl; and $R^{p2}$ is Benzoyl.

A suspension of the product from step 4(a) in acetonitrile is treated sequentially with water and glacial acetic acid, stirs at room temperature for 24 hours. The mixture is taken up in ethyl acetate and washed sequentially with 5% aqueous sodium carbonate and brine, dried ($MgSO_4$), filtered, and concentrated to provide the title compound.

Step 4(c): Compound 5 from Scheme 3, wherein R is —M—$R^1$, wherein —M— is —$CH_2$—CH=CH— and $R^1$ is Hydrogen; $R^P$ is Benzoyl; and $R^{p2}$ is Benzoyl.

A solution of the product from step 4(b) in ethanol/water (1:1) is treated with sodium nitrite (4 eq.), stirred at room temperature for 15 minute, treated with 4M HCl (4 eq.) over 15 minutes, heated to 70° C. for two hours, cooled to room temperature, diluted with ethyl acetate, washed sequentially with 5% aqueous sodium carbonate and brine, dried ($MgSO_4$), filtered, and concentrated. Purification of the residue by flash chromatography on silica gel with 98:1:1 dichloromethane:methanol:ammonium hydroxide provides the title compound.

Step 4(d): Compound 6 from Scheme 4, wherein V is —O—, R is —M—$R^1$, wherein —M— is —$CH_2$—CH=CH— and $R^1$ is Hydrogen; and $R^P$ is Benzoyl.

A suspension of the product from step 4(c) in ethanol/water (1:2) is treated with 1N HCl (10 eq.), stirred at 50° C. for 6 hours then cooled to 0° C. and made basic to pH~9–10 with 2N NaOH. The mixture is concentrated to remove most of ethanol and extracted with ethyl acetate. The organics are washed with brine and dried ($MgSO_4$). Removal of the solvents and purification on silica gel column provides the title compound.

Step 4(e): Compound 7 from Scheme 4, wherein V is —O—, R is —M—$R^1$, wherein —M— is —$CH_2$—CH=CH— and $R^1$ is Hydrogen; and $R^P$ is Benzoyl.

To the solution of NCS (1.7 eq.) in $CH_2Cl_2$ at −10° C. is added $Me_2S$ (2.5 eq.) dropwise. White precipitate is formed. Thirty minutes later the compound obtained from step 4(d) (1 eq.) in of $CH_2Cl_2$ is added slowly to the mixture over a 15 minutes period. The mixture is stirred for 40 minutes at −10° C. and $Et_3N$ was added. The mixture is taken up with ethyl acetate and is washed with $NaHCO_3$, brine, and dried over $Na_2SO_4$. Removal of the solvents and column chromatography with 10~25% acetone/hexanes gives the title compound.

Step 4(f): Compound 8 from Scheme 5, wherein R is —M—$R^1$, wherein —M— is —$CH_2$—CH=CH— and $R^1$ is Hydrogen; and $R^P$ is Benzoyl.

A solution of the product from step 4(e) (1 eq.) in THF and DMF at room temperature is treated with 1,1'-carbonyldiimidazole (3 eq.), cooled to 0° C., treated with sodium hydride (60% dispersion in mineral oil, 1.4 eq.) over 1 hour, stirred an additional 30 minutes at 0° C. and at room temperature for 2 days, diluted with ethyl acetate, washed sequentially with 5% aqueous sodium bicarbonate, water and brine, dried ($Na_2SO_4$), filtered, and concentrated to provide the title compound which was used without further purification in step 4(g).

Step 4(g): Compound of Formula (II): wherein W is Absent, $R^4$ is H; X is O; —M— is —$CH_2$—CH=CH— and $R^1$ is Hydrogen; and $R^P$ is Benzoyl.

A solution of the product from step 4(f) in acetonitrile at −78° C. is treated with liquid ammonia in a sealed reaction vessel, stirred at room temperature for 24 hours, concentrated first by evaporation of the ammonia at room temperature and atmospheric pressure, and concentrated finally to remove the acetonitrile. The crude product is purified by flash chromatography on silica gel with an acetone/hexanes mixture to give the title compound.

Step 4(h): Compound of formula (II): wherein W is Absent, $R^4$ is H; X is O; —M— is —$CH_2$—CH=CH— and $R^1$ is Hydrogen; and $R^P$ is Hydrogen.

A solution of a compound from $^4$(g) in methanol is heated at reflux for 4 hours. Removal of the solvent and column chromatography with 10% methanol/$CH_2Cl_2$ gives the title compound.

Example 5

Compound of Formula (II-A): wherein A is —NH—, X is O; —M— is —$CH_2$—CH=CH—; $R^2$ is 3-quinolyl; and $R^P$ is Hydrogen A slurry of the product from example 4, step 4(g), (0.20 mmol), 3-bromoquinoline (0.40 mmol), $Pd(OAc)_2$ (10 mg, 0.04 mmol), tri-o-tolylphosphine (18 mg, 0.060 mmol), and triethylamine (84 mL, 0.60 mmol) in degassed acetonitrile (2 mL) is heated at 90° C. in a sealed vessel for 24 hours. The reaction mixture is diluted with ethyl acetate and washed with 5% aqueous $NaHCO_3$ and brine, dried ($Na_2SO_4$), filtered, and concentrated. The crude residue is stirred in methanol at reflux for 4 hours, concentrated, and purified by flash column chromatography on silica gel with 90:10:0.5 dichloromethane/methanol/ammonium hydroxide to provide the title compound.

US 6,420,535 B1
39
What is claimed is:
1. A compound selected from the group consisting of:
a compound of the formula
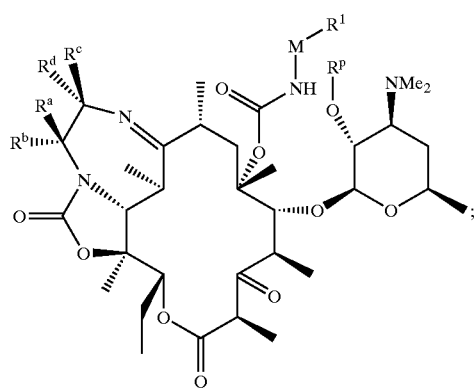
(I)
a compound of the formula
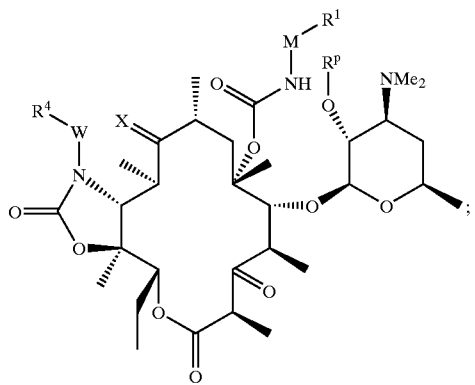
(II)
a compound of the formula
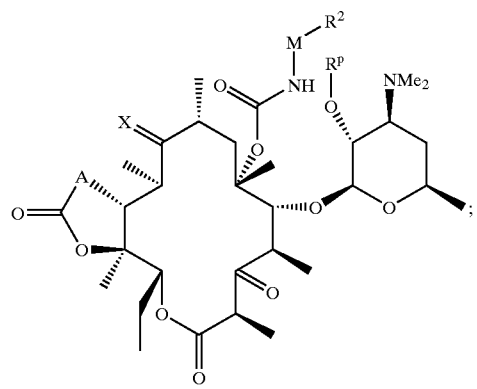
(II-A)
a compound of the formula
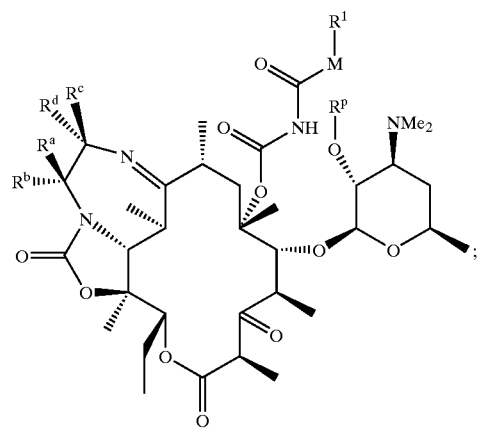
(III)
a compound of the formula
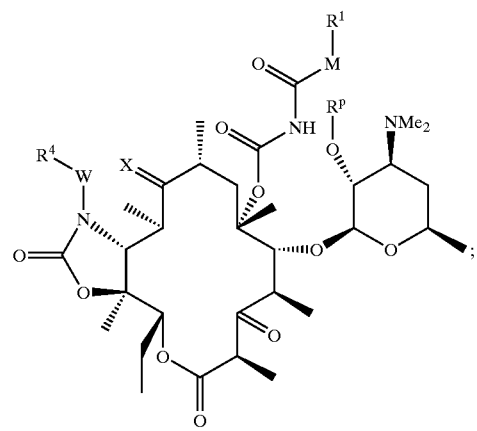
(IV)
a compound of the formula
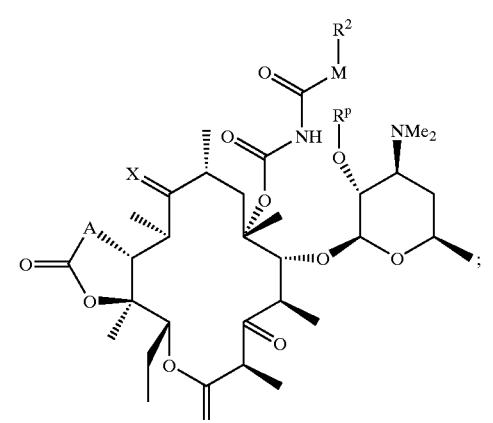
(IV-A)

a compound of the formula

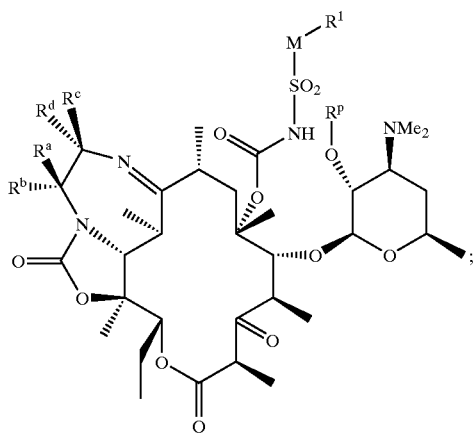

(V)

a compound of the formula

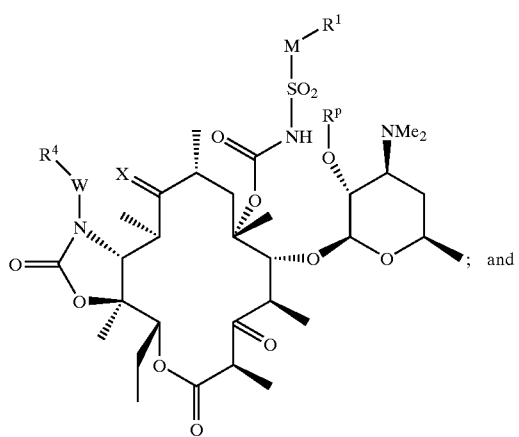

(VI)

a compound of the formula

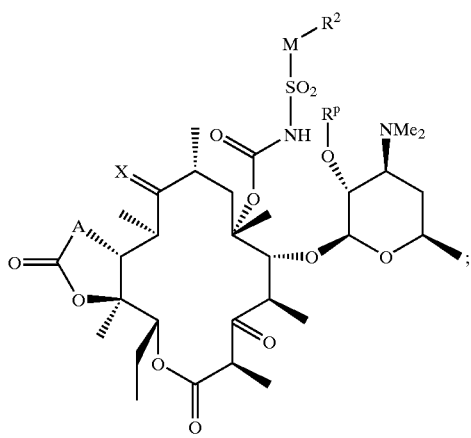

(VI-A)

or a pharmaceutically acceptable salt, solvate, ester, or prodrugs thereof, wherein:

$R^p$ is hydrogen or a hydroxy protecting group;

A is —O— or —NH—;

M is either absent or selected from the group consisting of:
  (a) —(CH$_2$)$_l$— where l is 1 to 5,
  (b) —(CH$_2$)$_m$—CH=CH— where m is 0 to 3,
  (c) —(CH$_2$)$_n$—C≡C— where n is 0 to 3;

$R^1$ is selected from the group consisting of:
  (a) hydrogen,
  (b) aryl,
  (c) substituted aryl,
  (d) heteroaryl,
  (e) substituted heteroaryl, and
  (f) Ar$_1$—Ar$_2$ wherein Ar$_1$ and Ar$_2$ are independently selected from the group consisting of:
    (i) aryl,
    (ii) substituted aryl,
    (iii) heteroaryl, and
    (iv) substituted heteroaryl;

$R^2$ is selected from the group consisting of:
  (a) aryl,
  (b) substituted aryl,
  (c) heteroaryl,
  (d) substituted heteroaryl, and
  (e) Ar$_1$—Ar$_2$ wherein Ar$_1$ and Ar$_2$ are independently selected from the group consisting of:
    (i) aryl,
    (ii) substituted aryl,
    (iii) heteroaryl, and
    (iv) substituted heteroaryl;

X is selected from the group consisting of:
  (a) O
  (b) N—OH
  (c) N—O—U—R$^3$ wherein U is selected from the group consisting of:
    (i) —C(O)—
    (ii) —C$_1$-C$_6$ alkyl,
    (iii) —C$_1$-C$_6$ alkenyl, and
    (iv) —C$_1$-C$_6$ alkynyl,
  and R$^3$ is selected from the group consisting of:
    (i) hydrogen,
    (ii) aryl,
    (iii) substituted aryl,
    (iv) heteroaryl,
    (v) substituted heteroaryl, and
    (vi) Ar$_1$—Ar$_2$ wherein Ar$_1$ and Ar$_2$ are independently selected from the group consisting of:
      (1) aryl,
      (2) substituted aryl,
      (3) heteroaryl, and
      (4) substituted heteroaryl;

W is selected from the group consisting of
  (a) —NH—(CH$_2$)$_p$— wherein p is 0 to 5,
  (b) —(CH$_2$)$_q$— wherein q is 0 to 5,
  (c) —O—(CH$_2$)$_r$—, wherein r is 0 to 5,
  d) —NH—C$_1$-C$_6$ alkenyl-,
  (e) —C$_1$-C$_6$ alkenyl-,
  (f) —O—C$_1$-C$_6$ alkenyl-,
  (g) —NH—C$_1$-C$_6$ alkynyl-,
  (h) —C$_1$-C$_6$ alkynyl-, and
  (i) —O-C$_1$-C$_6$ alkynyl-, $R^4$ is selected from the group consisting of:
  (a) hydrogen,
  (b) aryl,
  (c) substituted aryl,
  (d) heteroaryl,
  (e) substituted heteroaryl, and
  (f) Ar$_1$—Ar$_2$ wherein Ar$_1$ and Ar$_2$ are independently selected from the group consisting of:

(i) aryl,
(ii) substituted aryl,
(iii) heteroaryl, and
(iv) substituted heteroaryl; and $R^a$, $R^b$, $R^c$ and $R^d$ are independently selected from the group consisting of:
(a) hydrogen;
(b) $C_1$–$C_6$ alkyl, optionally substituted with one or more substituents selected from the group consisting of:
  (i) —L—M—$R^1$ or —L—M—$R^2$, wherein M, $R^1$, and $R^2$ are as defined above, and L is either absent or selected from the group consisting of:
    (1) —C(O)NH—;
    (2) —NHC(O)—;
    (3) —NH—;
    (4) —N(CH$_3$)—;
    (5) —O—;
    (6) —S(O)$_x$—, wherein x is 0, 1, or 2;
    (7) —C(=NH)NH—;
    (8) —C(O)O—;
    (9) —OC(O)—;
    (10) —OC(O)NH—;
    (11) —NHC(O)O—; and
    (12) —NHC(O)NH—; and
  (ii) halogen;
(C) $C_3$–$C_7$ cycloalkyl;
(d) heterocycloalkyl; and
(e) substituted heterocycloalkyl; or any one pair of substituents selected from the group consisting of $R^aR^b$, $R^aR^c$, $R^aR^d$, $R^bR^c$, $R^bR^d$ or $R^cR^d$ taken together with the atom or atoms to which they are they are attached form a 3- to 7- membered ring optionally containing a hetero function selected from the group consisting of —O—; —NH—; —N($C_1$–$C_6$ alkyl-)—;
—N(aryl-$C_1$–$C_6$ alkyl-)—; —N(substituted aryl-$C_1$–$C_6$ alkyl-)—; —N(heteroaryl-$C_{1-C6}$ alkyl-)—; —N(substituted heteroaryl-$C_1$–$C_6$ alkyl-)—; —S(O)$_x$ —, wherein x is 0, 1, or 2; —C(O)—NH—; —NH—C(O)—; —C(O)—NR$^{12}$—; and —NR$^{12}$—C(O)—; wherein R$^{12}$ is hydrogen, $C_1$–$C_3$ alkyl, $C_1$–$C_3$ alkyl substituted with aryl, substituted aryl, heteroaryl, or substituted heteroaryl.

2. A compound according to claim 1, represented by the formula:

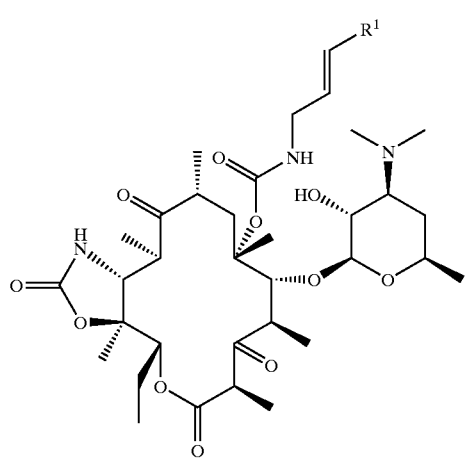

(IX)

wherein $R^1$ is as defined above in claim 1.

3. A compound according to claim 1, represented by the formula:

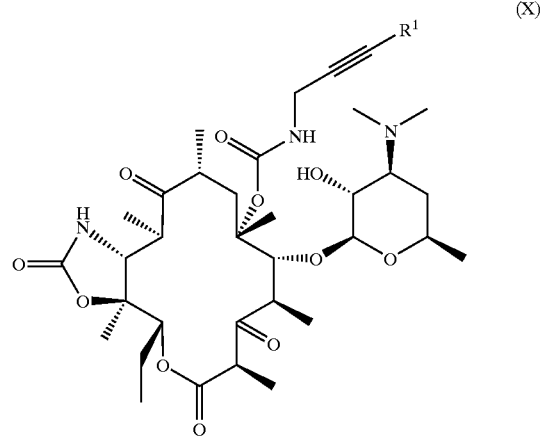

(X)

wherein $R^1$ is as defined above in claim 1.

4. A compound according to claim 1, represented by the formula:

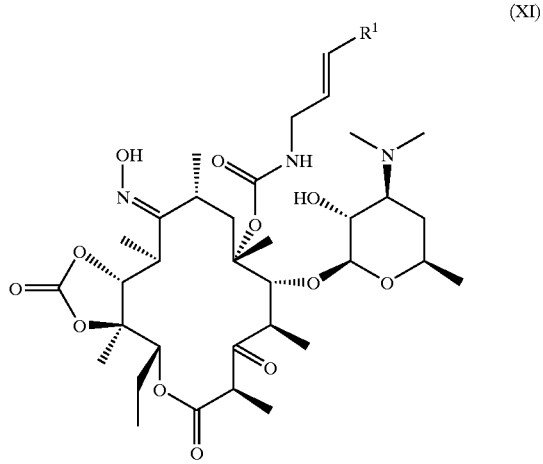

(XI)

wherein $R^1$ is as defined above in claim 1.

5. A compound according to claim 1, represented by the formula:

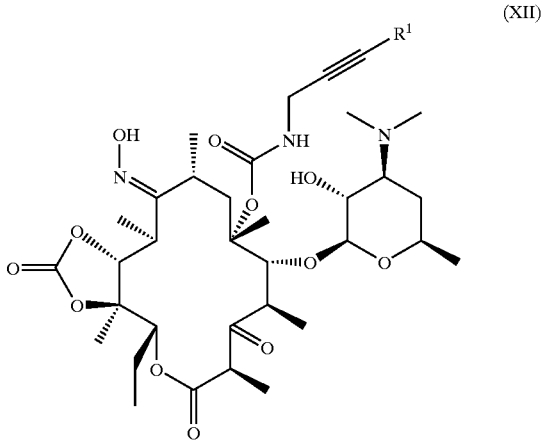

(XII)

wherein $R^1$ is as defined above in claim 1.

6. A compound according to claim 1, represented by the formula:

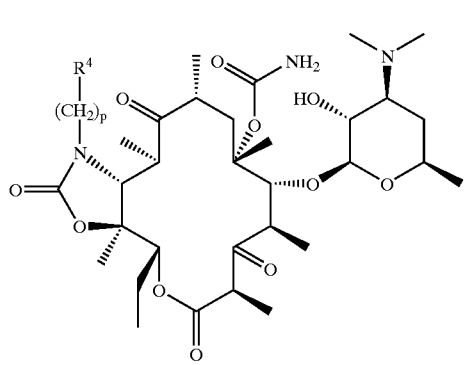
(XIII)

wherein $R^4$ is as defined above in claim 1 and p is 0 to 5.

7. A compound according to claim 1, represented by a formula:

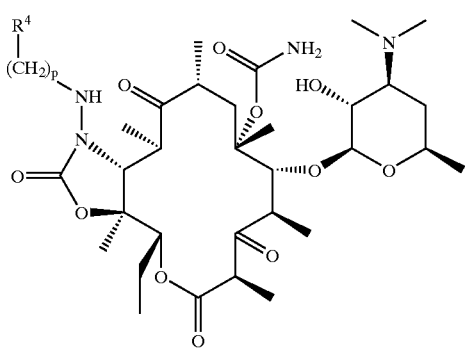
(XIV)

wherein $R^4$ is as defined above in claim 1 and p is 0 to 5.

8. A compound according to claim 1, selected from the group consisting of:

Compound of formula (IV-A): wherein A is —O—; X is N—OH; —M— is absent; $R^2$ is phenyl; and Rp is hydrogen;

Compound of formula (II-A): wherein A is —O—; X is N—OH; —M— is absent; $R^2$ is hydrogen; and $R^p$ is hydrogen;

Compound of formula (II-A): wherein A is —O—; X is N—OH; —M— is —CH$_2$—CH=CH—; $R^2$ is 3-quinolyl; and $R^p$ is hydrogen;

Compound of formula (II): wherein W is absent, $R^4$ is H; X is O; —M— is —CH$_2$—CH=CH— $R^1$ is hydrogen; and $R^1$ is hydrogen; and Compound of formula (II-A): wherein A is —NH—; X is O; —M— is —CH$_2$—CH=CH—; $R^2$ is 3-quinolyl; and $R^p$ is hydrogen.

9. A process for preparing a compound selected from the group consisting of:

a compound of the formula

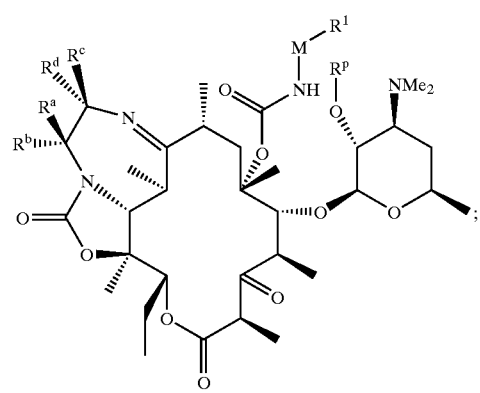
(I)

a compound of the formula

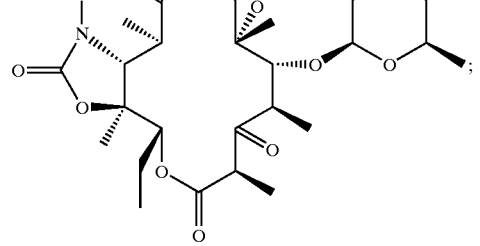
(II)

a compound of the formula

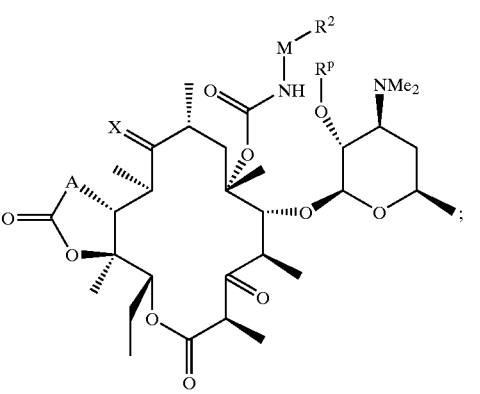
(II-A)

a compound of the formula
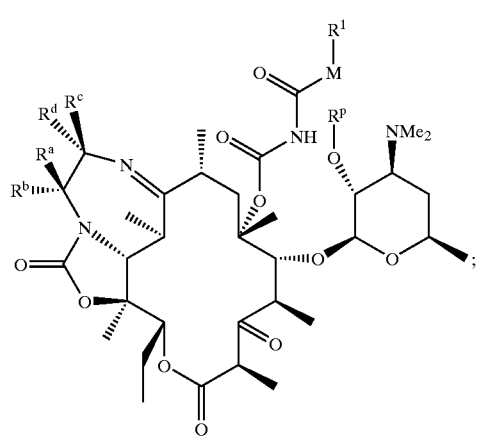
(III)
a compound of the formula
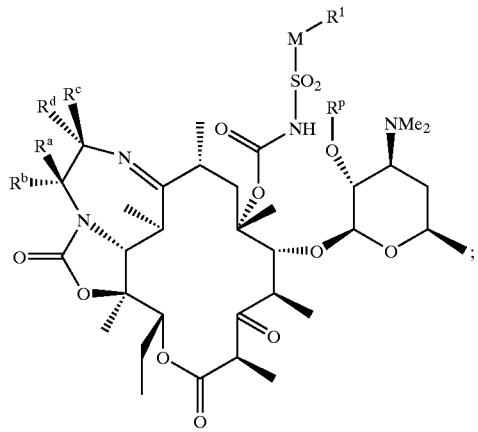
(V)
a compound of the formula
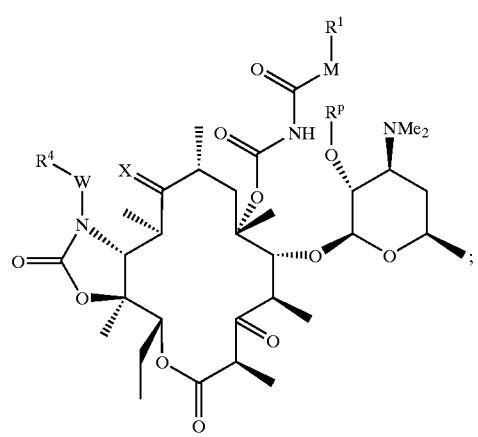
(IV)
a compound of the formula
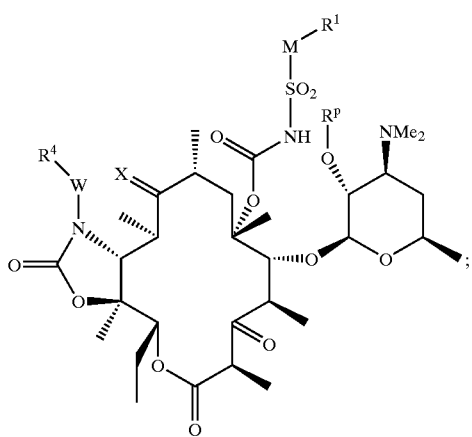
(VI)
a compound of the formula
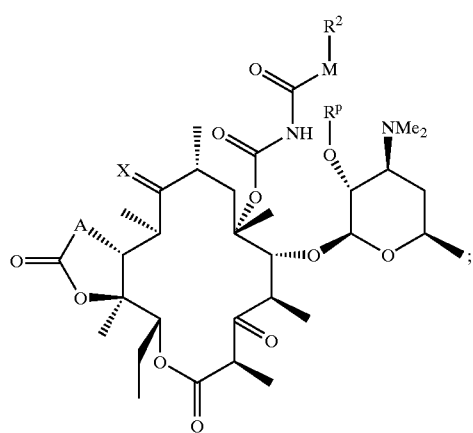
(IV-A)
a compound of the formula
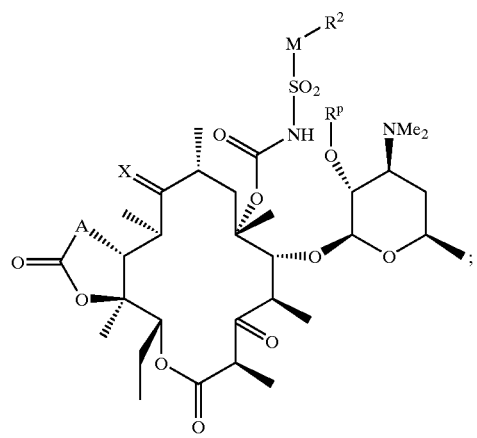
(VI-A)
or a pharmaceutically acceptable salt, solvate, ester, or prodrugs thereof, wherein:

$R^p$ is hydrogen or a hydroxy protecting group;

A is —O— or —NH—;

M is either absent or selected from the group consisting of:
(a) —(CH$_2$)$_l$— where l is 1 to 5,
(b) —(CH$_2$)$_m$—CH=CH— where m is 0 to 3,
(c) —(CH$_2$)$_n$—C≡C— where n is 0 to 3;

$R^1$ is selected from the group consisting of:
(a) hydrogen,
(b) aryl,
(c) substituted aryl,
(d) heteroaryl,
(e) substituted heteroaryl, and
(f) Ar$_1$—Ar$_2$ wherein Ar$_1$ and Ar$_2$ are independently selected from the group consisting of:
  (i) aryl,
  (ii) substituted aryl,
  (iii) heteroaryl, and
  (iv) substituted heteroaryl;

$R^2$ is selected from the group consisting of:
(a) aryl,
(b) substituted aryl,
(c) heteroaryl,
(d) substituted heteroaryl, and
(e) Ar$_1$—Ar$_2$ wherein Ar$_1$ and Ar$_2$ are independently selected from the group consisting of:
  (i) aryl,
  (ii) substituted aryl,
  (iii) heteroaryl, and
  (iv) substituted heteroaryl;

X is selected from the group consisting of:
(a) O
(b) N—OH
(c) N—O—U—$R^3$ wherein U is selected from the group consisting of:
  (i) —C(O)—
  (ii) —C$_1$–C$_6$ alkyl,
  (iii) —C$_1$–C$_6$ alkenyl, and
  (iv) —C$_1$–C$_6$ alkynyl,
and $R^3$ is selected from the group consisting of:
  (i) hydrogen,
  (ii) aryl,
  (iii) substituted aryl,
  (iv) heteroaryl,
  (v) substituted heteroaryl, and
  (vi) Ar$_1$—Ar$_2$ wherein Ar$_1$ and Ar$_2$ are independently selected from the group consisting of:
    (1) aryl,
    (2) substituted aryl,
    (3) heteroaryl, and
    (4) substituted heteroaryl;

W is selected from the group consisting of
(a) —NH—(CH$_2$)$_p$— wherein p is 0 to 5,
(b) —(CH$_2$)$_q$— wherein q is 0 to 5,
(c) —O—(CH$_2$)$_r$— wherein r is 0 to 5,
(d) —NH—C$_1$–C$_6$ alkenyl-,
(e) —C$_1$–C$_6$ alkenyl-,
(f) —O—C$_1$–C$_6$ alkenyl-,
(g) —NH—C$_1$–C$_6$ alkynyl-,
(h) —C$_1$–C$_6$ alkynyl-, and
(i) —O—C$_1$–C$_6$ alkynyl-, $R^4$ is selected from the group consisting of:
(a) hydrogen,
(b) aryl,
(c) substituted aryl,
(d) heteroaryl,
(e) substituted heteroaryl, and
(f) Ar$_1$—Ar$_2$ wherein Ar$_1$ and Ar$_2$ are independently selected from the group consisting of:
  (i) aryl,
  (ii) substituted aryl,
  (iii) heteroaryl, and
  (iv) substituted heteroaryl; and $R^a$, $R^b$, $R^c$ and $R^d$ are independently selected from the group consisting of:
(a) hydrogen;
(b) C$_1$–C$_6$ alkyl, optionally substituted with one or more substituents selected from the group consisting of:
  (i) —L—M—R$^1$ or —L—M—R$^2$, wherein M, R$^1$, and R$^2$ are as defined above, and L is either absent or selected from the group consisting of:
    (1) —C(O)NH—;
    (2) —NHC(O)—;
    (3) —NH—;
    (4) —N(CH$_3$)—;
    (5) —O—;
    (6) —S(O)$_x$—, wherein x is 0, 1, or 2;
    (7) —C(=NH)NH—;
    (8) —C(O)O—;
    (9) —OC(O)—;
    (10) —OC(O)NH—;
    (11) —NHC(O)O—; and
    (12) —NHC(O)NH—; and
  (ii) halogen;
(C) C$_3$–C$_7$ cycloalkyl;
(d) heterocycloalkyl; and
(e) substituted heterocycloalkyl;

or any one pair of substituents selected from the group consisting of $R^aR^b$, $R^aR^c$, $R^aR^d$, $R^bR^c$, $R^bR^d$ or $R^cR^d$ taken together with the atom or atoms to which they are form a 3- to 7- membered ring optionally containing a hetero function selected from the group consisting of —O—; —NH—; —N(C$_1$-C$_6$ alkyl-)—; —N(aryl-C$_1$-C$_6$ alkyl-)—; —N(substituted aryl-C$_1$-C$_6$ alkyl-)—; —N(heteroaryl-C$_1$-C$_6$ -alkyl-)—; —N(substituted heteroaryl-C$_1$-C$_6$ alkyl-)—; —S(O)$_x$—, wherein x is 0, 1, or 2; —C(O)—NH—; —NH—C(O)—; —C(O)—NR$^{12}$—; and —NR$^{12}$—C(O)—; wherein R$^{12}$ is hydrogen, C$_1$–C$_3$ alkyl, C$_1$–C$_3$ alkyl substituted with aryl, substituted aryl, heteroaryl, or substituted heteroaryl; comprising the steps of:

(a) reacting a compound having a formula:

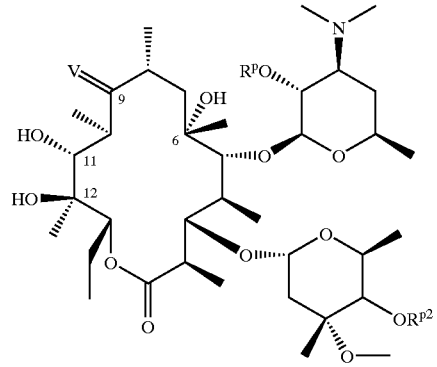

wherein V is selected from the group consisting of:
(i) O,
(ii) N—O—(CH$_2$)$_s$—R$^x$, wherein s is 0 to 5 and R$^x$ is selected from the group consisting of:

(1) hydrogen,
(2) alkyl,
(3) substituted alkyl,
(4) aryl,
(5) substituted aryl,
(6) heteroaryl, and
(7) substituted heteroaryl,
(iii) N—O—C(O)—(CH$_2$)$_s$—R$^x$, wherein s and R$^x$ is as defined above,
(iv) N—O—C(R$^y$)(R$^z$)—O—R$^x$, wherein R$^x$ is as defined above, and R$^y$ and R$^z$ are independently selected from the group consisting of:
(5) hydrogen,
(6) unsubstituted C$_1$–C$_{12}$-alkyl,
(7) C$_1$–C$_{12}$-alkyl substituted with aryl, and
(8) C$_1$–C$_{12}$-alkyl substituted with substituted aryl, or R$^y$ and R$^z$ taken together with the carbon to which each is attached form a C$_3$–C$_{12}$-cycloalkyl ring; and R$^p$ and R$^{p2}$ are as defined above; with either (i) an isocyanate reagent of the formula O=C=N—M—R$^1$, O=C=N—M—R$^2$, O=C=N—C(O)—M—R$^1$, O=C=N—C(O)—M—R$^2$, O=C=N—S(O)$_2$—M—R$^1$, or O=C=N—S(O)$_2$—M—R$^2$, wherein M, R$^1$, and R$^2$ are as defined above, or (ii) an activated isocyanate derivative followed by alkylation with a compound of the formula X$_1$—M—R$^1$ or X$_1$—M—R$^2$, wherein M, R$^1$, and R$^2$ are as defined above and X$_1$ is a halide or a leaving group, and optionally removing the activating group;
(b) carrying out one or more of the following steps in any suitable order:
(i) removing any hydroxy protecting group that may be present;
(ii) removing a protecting group on the C9-oxime;
(iii) converting the C9-oxime into a keto moiety;
(iv) removing the cladinose sugar and oxidizing the resulting hydroxy group;
(v) converting the 11,12-diol into an 11,12-carbonate;
(vi) converting the 11,12-diol into an 11,12-carbamate optionally substituted on the nitrogen atom; and
(vi) preparing a tricyclic imine derivative from the 11,12-carbamate.

10. A process according to claim 9, wherein the 11,12-carbonate is prepared by treating the compound of the formula:

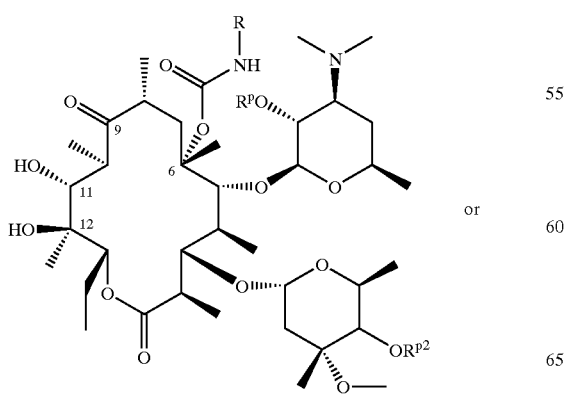

or

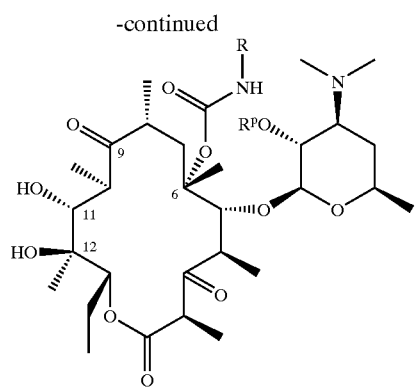

wherein R is selected from the group consisting of —M—R$^1$, —M—R$^2$, —C(O)—M—R$^1$, —C(O)—M—R$^2$, —S(O)$_2$—M—R$^1$, —S(O)$_2$—M—R$^2$, with carbonyldiimidazole and sodium hexamethyldisilazide and optionally removing the 2'-hydroxy group.

11. A process according to claim 9, wherein the 11,12-carbamate optionally substituted on the nitrogen atom is prepared by the steps of:
(a) treating the compound of the formula:

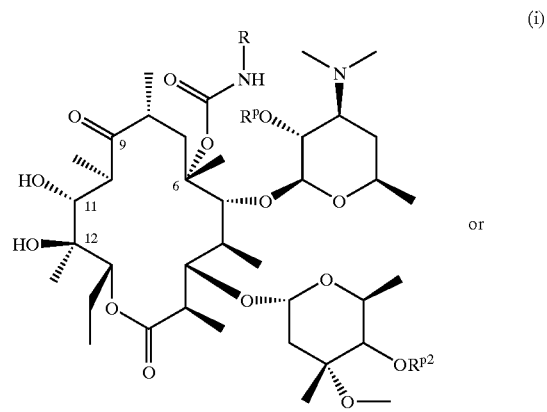

or

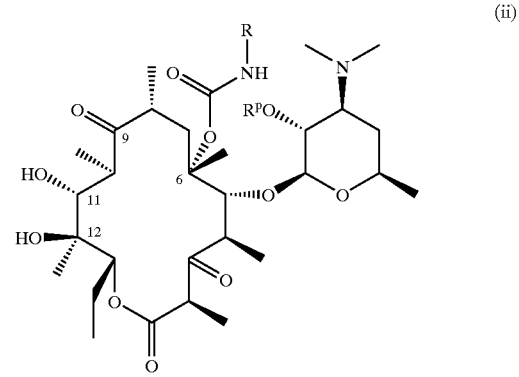

wherein R is selected from the group consisting of —M—R$^1$, —M—R$^2$, —C(O)—M—R$^1$, —C(O)—M—R$^2$, —S(O)$_2$—M—R$^1$, —S(O)$_2$—M—R$^2$, optionally with a reagent combination selected from the group consisting of:
(1) an alkali metal hydride and a phosgene reagent selected from phosgene, diphosgene and triphosgene under anhydrous conditions, followed by a base catalyzed decarboxylation, and
(2) reaction with methanesulfonic anhydride in pyridine, followed by treatment with an amine base, (b) treating the compound of formula (i) or (ii) or the compound obtained in step (a) with an alkali metal hydride base and carbonyldiimidazole;

(c) reacting the compound obtained in step (b) with an amine of the formula $H_2N$—W—$R^4$, wherein W and $R^4$ are as defined above, anhydrous ammonia, or ammonium hydroxide;

(d) optionally removing the cladinose sugar and oxidizing the resulting hydroxy group;

(e) optionally removing any hydroxy protecting group that may be present.

12. A process according to claim 11, wherein the tricyclic imine is prepared by the steps of:

(a) treating a compound of the formula:

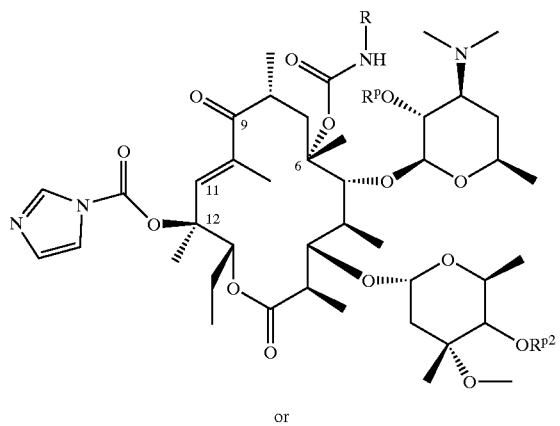

or

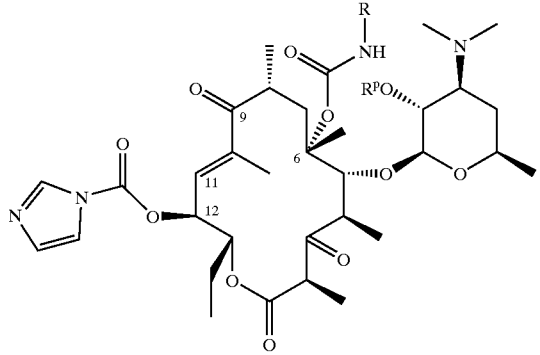

wherein R is as defined above, with a diamine of the formula:

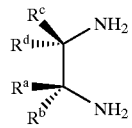

wherein $R^a$, $R^b$, $R^c$ and $R^d$ are as defined in claim 9;

(b) cyclizing the compound obtained in step (a);

(c) optionally removing the cladinose sugar and oxidizing the resulting hydroxy group;

(d) optionally removing any hydroxy protecting group that may be present.

13. A pharmaceutical composition comprising a compound of claim 1 and a pharmaceutically acceptable carrier.

14. A method of treating a bacterial infection comprising administering a therapeutically effective amount of a compound in claim 1 to a patient in need of such treatment.

* * * * *